(12) United States Patent
McNeill et al.

(10) Patent No.: US 8,362,942 B2
(45) Date of Patent: Jan. 29, 2013

(54) MOVING-ENTITY DETECTION

(75) Inventors: James McNeill, Orlando, FL (US); Todd MacKey, Satellite Beach, FL (US); Tim Dyson, Melbourne, FL (US)

(73) Assignee: L-3 Communications CyTerra Corporation, Orlando, FL (US)

( * ) Notice: Subject to any disclaimer, the term of this patent is extended or adjusted under 35 U.S.C. 154(b) by 536 days.

(21) Appl. No.: 12/391,940

(22) Filed: Feb. 24, 2009

(65) Prior Publication Data

US 2009/0262006 A1    Oct. 22, 2009

Related U.S. Application Data

(63) Continuation-in-part of application No. 12/029,481, filed on Feb. 12, 2008, which is a continuation of application No. 11/428,956, filed on Jul. 6, 2006, now Pat. No. 7,345,618, which is a continuation of application No. 11/279,859, filed on Apr. 14, 2006, now abandoned.

(60) Provisional application No. 60/671,105, filed on Apr. 14, 2006, provisional application No. 61/031,113, filed on Feb. 25, 2008.

(51) Int. Cl.
    *G01S 13/52*     (2006.01)
    *G01S 13/524*    (2006.01)
(52) U.S. Cl. ............................... 342/22; 342/28
(58) Field of Classification Search ............ 342/22, 342/27, 28
    See application file for complete search history.

(56) References Cited

U.S. PATENT DOCUMENTS

| | | | |
|---|---|---|---|
| 5,345,240 A | 9/1994 | Frazier | |
| 5,357,253 A | 10/1994 | Van Etten et al. | |
| 5,446,461 A | 8/1995 | Frazier | |
| 5,861,837 A | 1/1999 | Richardson et al. | |
| 5,905,455 A | 5/1999 | Heger | |
| 6,278,401 B1 | 8/2001 | Wigren | |
| 6,417,797 B1 * | 7/2002 | Cousins et al. | 342/27 |
| 6,466,155 B2 | 10/2002 | Taylor et al. | |
| 6,512,976 B1 | 1/2003 | Sabatino et al. | |
| 6,970,128 B1 | 11/2005 | Dwelly et al. | |

(Continued)

FOREIGN PATENT DOCUMENTS

| | | |
|---|---|---|
| GB | 2249448 A | 5/1992 |
| WO | WO2008001092 A3 | 5/2008 |

(Continued)

OTHER PUBLICATIONS

Office Action issued in U.S. Appl. No. 11/428,956 mailed Aug. 10, 2007, 6 pages.

(Continued)

*Primary Examiner* — Ian Lobo
(74) *Attorney, Agent, or Firm* — Fish & Richardson P.C.

(57) ABSTRACT

A system and method for detecting entities based on movement can involve transmission circuitry configured to enable transmission of a stepped-frequency radar signal, an antenna, and receiving circuitry configured to generate data including information associated with frequency and phase shifts between the transmitted signal and the reflections of the transmitted signal. The system also can involve a processor configured to analyze the generated data to determine information associated with a moving object located at a side of a wall different than a side of the wall of which the system is located. The analyzing can involve compensating for the effect of motion of the system on the phase shifts between the transmitted signal and the reflections of the transmitted signal.

39 Claims, 21 Drawing Sheets

U.S. PATENT DOCUMENTS

| | | | |
|---|---|---|---|
| 7,180,441 | B2 | 2/2007 | Rowe et al. |
| 7,212,149 | B2 * | 5/2007 | Abatzoglou ............... 342/25 F |
| 7,307,575 | B2 | 12/2007 | Zemany |
| 7,345,618 | B1 | 3/2008 | Cole et al. |
| 7,920,088 | B2 | 4/2011 | Thompson et al. |
| 2004/0232329 | A1 | 11/2004 | Biggs |
| 2005/0128123 | A1 | 6/2005 | Greneker et al. |
| 2005/0128124 | A1 | 6/2005 | Greneker et al. |
| 2005/0270219 | A1 | 12/2005 | Dwelly et al. |
| 2006/0025897 | A1 | 2/2006 | Shostak et al. |
| 2006/0028369 | A1 | 2/2006 | Rausch et al. |
| 2006/0061504 | A1 | 3/2006 | Leach et al. |
| 2006/0170584 | A1 | 8/2006 | Romero et al. |
| 2006/0250294 | A1 | 11/2006 | Zemany et al. |
| 2007/0024488 | A1 | 2/2007 | Zemany et al. |
| 2007/0171119 | A1 | 7/2007 | Dwelly et al. |
| 2007/0205937 | A1 | 9/2007 | Thompson et al. |
| 2009/0087029 | A1 | 4/2009 | Coleman et al. |
| 2009/0195435 | A1 | 8/2009 | Kapilevich et al. |
| 2009/0262005 | A1 | 10/2009 | McNeill et al. |
| 2009/0295618 | A1 | 12/2009 | Beeri et al. |

FOREIGN PATENT DOCUMENTS

| | | |
|---|---|---|
| WO | WO 2009/139940 | 11/2009 |
| WO | WO 2009/139941 | 11/2009 |

OTHER PUBLICATIONS

Office Action issued in U.S. Appl. No. 11/428,956 mailed Nov. 20, 2006, 7 pages.

PCT International Search Report and Written Opinion issued in PCT International Application No. PCT/US09/35009 dated Oct. 23, 2009.

PCT International Search Report and Written Opinion issued in PCT International Application No. PCT/US09/35007 dated Oct. 21, 2009.

U.S. Appl. No. 11/279,859, filed Apr. 14, 2006, 41 pages.

U.S. Appl. No. 12/029,481, filed Feb. 12, 2008, 34 pages.

U.S. Appl. No. 60/671,105, filed Apr. 14, 2005, 17 pages.

U.S. Appl. No. 61/031,113, filed Feb. 25, 2008, 33 pages.

Office Action issued in U.S. Appl. No. 11/279,859 mailed Nov. 20, 2006, 7 pages.

Tavakolian, K., et al., "Development of a Novel Contactless Mechanocardiograph Device," International Journal of Telemedicine and Applications, vol. 2008, Article ID 436870, 5 pages, Hindawi Publishing Corporation, Mar. 3, 2008.

International Search Report and Written Opinion for International Application No. PCT/US2010/061005, mailed Feb. 17, 2011, 16 pages.

Office Action for U.S. Appl. No. 12/391,909, mailed Jul. 27, 2011, 18 pages.

Communication regarding European Search Report for European Applicaiton No. 09747027.2, mailed Feb. 6, 2012, 3 pages.

Office Action for U.S. Appl. No. 12/391,909, mailed Jan. 12, 2012, 16 pages.

Office Action for U.S. Appl. No. 12/029,481, mailed Dec. 29, 2011, 7 pages.

European Search Report for European Application No. 09747026.4, mailed Apr. 23, 2012, 3 pages.

Communication pursuant to Article 94(3) EPC for European Application No. 09747027.2, mailed Apr. 17, 2012, 5 pages.

Communication pursuant to Article 94(3) EPC for European Application No. 09747026.4, mailed May 15, 2012, 4 pages.

* cited by examiner

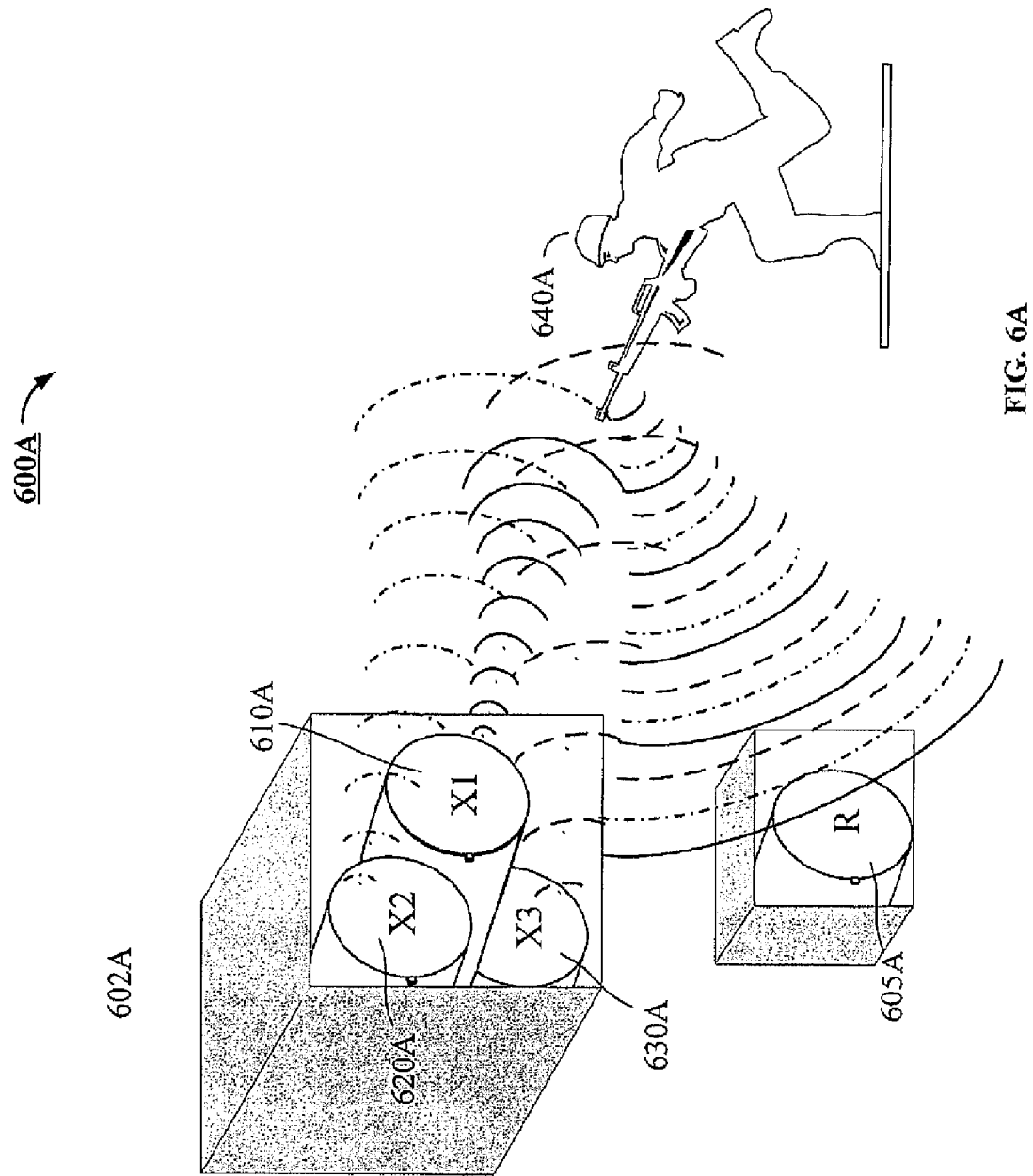

MOVING-ENTITY DETECTION

CROSS-REFERENCES TO RELATED APPLICATIONS

This application claims priority to U.S. Provisional Application No. 61/031,113, which was filed on Feb. 25, 2008 and titled "Moving-Entity Detection," and this application is a continuation-in-part of U.S. application Ser. No. 12/029,481, filed Feb. 12, 2008, and titled "Moving-Entity Detection," which is a continuation of U.S. application Ser. No. 11/428,956, filed Jul. 6, 2006, now U.S. Pat. No. 7,345,618 B1, issued Mar. 18, 2008 and titled "Moving-Entity Detection," which is a continuation of U.S. application Ser. No. 11/279,859, filed Apr. 14, 2006, and titled "Moving-Entity Detection," abandoned, which claims priority to U.S. Provisional Application No. 60/671,105, filed Apr. 14, 2005, and titled "Wall Penetrating Personnel Detection Sensor (WPPDS)," expired, all of which are incorporated by reference in their entirety.

STATEMENT REGARDING FEDERALLY SPONSORED RESEARCH OR DEVELOPMENT

The U.S. Government may have certain rights in this invention as provided for in the terms under agreement number W15P7T-05-9-P232 awarded by DARPA and the US Army Communications-Electronics Command.

TECHNICAL FIELD

This description relates to detecting moving entities, such as detecting the presence of a moving person concealed behind a wall in a building.

BACKGROUND

Detection sensors may be used to determine the presence of objects when visual recognition is difficult.

SUMMARY

In general, in some aspects, a method for detecting entities based on movement includes transmitting a stepped-frequency radar signal from a first side of a wall to a second side of the wall and detecting reflections of the transmitted signal with an antenna while the antenna is in motion. The method also includes determining one or more characteristics of motion of a system which includes the antenna during the detection of reflections of the transmitted signal. The method further includes generating data including information associated with frequency and phase shifts between the transmitted signal and the reflections of the transmitted signal detected with the antenna while the antenna is in motion. The method additionally includes analyzing the generated data to determine information associated with a moving object located beyond the second side of the wall. The analyzing includes using the determined one or more characteristics of the motion of the system to compensate for the effect of the motion of the system on the phase shifts between the transmitted signal and the reflections of the transmitted signal.

This and other implementations can optionally include one or more of the following features, which also may optionally be in any combination. In the method, determining the one or more characteristics of the motion of the system during the detection of reflections of the transmitted signal can include receiving an indication of the one or more characteristics of the motion of the system from a motion sensor included within the system. Receiving an indication of the one or more characteristics of the motion of the system from the motion sensor can include receiving information from a global positioning system sensor. Receiving an indication of the one or more characteristics of the motion of the system from the motion sensor can include receiving information from an inertial sensor. Receiving information from an inertial sensor can include sampling one or more outputs of the inertial sensor indicating a current state of acceleration in each of three spatial dimensions.

Also, generating the data can include generating packets of data which each include information associated with the received indication of the one or more characteristics of the motion of the system along with the information associated with frequency and phase shifts. Using the determined one or more characteristics of the motion of the system to compensate for the effect of the motion can include deriving the motion of the system from the received indication of the one or more characteristics of the motion of the system from the motion sensor, altering the generated data to reverse the Doppler shift of the detected reflections resulting from the derived motion of the system, and analyzing the altered data to determine the information associated with the moving object located beyond the second side of the wall.

The method can also include identifying a phase change of detected reflections of the transmitted signal from stationary objects or scattering and the one or more characteristics of the motion of the system can be determined based on the identification of the phase change of detected reflections of the transmitted signal from stationary objects or scattering. Identifying the phase change of detected reflections of the transmitted signal from stationary objects or scattering can include determining that the detected reflections are reflected from an object that had previously reflected transmission which was not indicative of movement. Identifying the phase change of detected reflections of the transmitted signal from stationary objects or scattering can include identifying phase changes indicative of a consistency of movement or a pattern of movement of scattering or objects. Using the determined one or more characteristics of the motion of the system to compensate for the effect of the motion can include deriving the motion of the system from the one or more characteristics of the motion of the system, altering the generated data to reverse the Doppler shift of the detected reflections resulting from derived motion of the system, and analyzing the altered data to determine the information associated with the moving object located beyond the second side of the wall.

Further, transmitting the stepped-frequency radar signal can include beginning transmission of the stepped-frequency radar signal at a first system location and moving the system during transmission of the stepped-frequency radar signal from the first system location to a second system location. Detecting reflections of the transmitted signal with the antenna while the antenna is in motion can include detecting reflections of the transmitted signal during the movement of the antenna from the first system location to the second system location. Analyzing the generated data can include determining the information associated with the moving object located beyond the second side of the wall based upon the reflections detected during the movement of the antenna from the first system location to the second system location.

Moreover, generating the data can include generating data for detected reflections which includes information associated with frequency and phase shifts and associated with the one or more characteristics of the motion of the system determined during the detection of reflections of the transmitted signal. Analyzing the generated data can include generating a synthetic aperture radar image using the data including information associated with frequency and phase shifts and associated with the one or more characteristics of the motion of the system. Determining the one or more characteristics of the motion of the system during the detection of reflections of the transmitted signal can include sampling output of an inertial sensor within the system. Generating the data can include generating a packet of data for reflections received at each of multiple system locations between the first and second system locations, each packet including the information associated with frequency and phase shifts, and output of the sampled inertial sensor at the time the reflection was detected.

In addition, the method can include identifying a transmit-to-receive leakage signal resulting from the transmission of the stepped-frequency radar signal, generating a cancellation waveform configured to remove effects of the identified transmit-to-receive leakage signal, and using the generated cancellation waveform to remove effects of transmit-to-receive leakage signal of subsequent transmissions. The method can also include, after transmitting the stepped-frequency radar signal, determining the stepped-frequency radar signal should be altered, generating an altered stepped-frequency radar signal such that the order of the transmitted frequencies is changed or such that one or more of the transmitted frequencies is removed, and transmitting the altered stepped-frequency radar signal. Determining the one or more characteristics of the motion of the system can include determining one or more characteristics of the motion of the antenna.

In other implementations, some aspects include a system for detecting entities based on movement. The system includes transmission circuitry configured to enable transmission of a stepped-frequency radar signal and an antenna configured to detect reflections of the transmitted signal. The system also includes receiving circuitry configured to receive detected reflections from the antenna and to generate data including information associated with frequency and phase shifts between the transmitted signal and the reflections of the transmitted signal. The system further includes a processor configured to receive the generated data from the receiving circuitry and to analyze the generated data to determine information associated with a moving object located at a side of a wall different than a side of the wall of which the system is located. The analyzing includes using one or more characteristics of motion of the system to compensate for the effect of the motion of the system on the phase shifts between the transmitted signal and the reflections of the transmitted signal.

This and other implementations can optionally include one or more of the following features, which also may optionally be in any combination. The receiving circuitry can be a part of the processor. The system can includes a motion sensor configured to determine the one or more characteristics of the motion of the system and, to generate the data, the receiving circuitry can be configured to receive an indication of the determined one or more characteristics of the motion of the system from the motion sensor. The motion sensor can be a global positioning system sensor. The motion sensor can be an inertial sensor. The inertial sensor can be configured to output a current state of acceleration in each of three spatial dimensions. To generate the data, the receiving circuitry can be configured to generate packets of data which each include information associated with the received indication of the determined one or more characteristics of the motion of the system along with the information associated with frequency and phase shifts.

Also, to use the one or more characteristics of the motion of the system to compensate for the effect of the motion, the processor can be configured to derive the motion of the system from the received indication of the one or more characteristics of the motion of the system from the motion sensor, alter the generated data to reverse the Doppler shift of the detected reflections resulting from the derived motion of the system, and analyze the altered data to determine the information associated with the moving object at the side of the wall different than the side of the wall of which the system is located. To use the one or more characteristics of the motion of the system to compensate for the effect of the motion, the processor can be configured to identify a phase change of detected reflections of the transmitted signal from stationary objects or scattering and determine the one or more characteristics of the motion of the system based on the identification of the phase change of detected reflections of the transmitted signal from stationary objects or scattering.

Further, to identify the phase change of detected reflections of the transmitted signal from stationary objects or scattering, the processor can be configured to determine that the detected reflections are reflected from an object that had previously reflected transmission which was not indicative of movement. To identify the phase change of detected reflections of the transmitted signal from stationary objects or scattering, the processor can be configured to identify phase changes indicative of a consistency of movement or a pattern of movement of scattering or objects. To use the determined one or more characteristics of the motion of the system to compensate for the effect of the motion, the processor can be configured to derive the motion of the system from the one or more characteristics of the motion of the system, alter the generated data to reverse the Doppler shift of the detected reflections resulting from the derived motion of the system, and analyze the altered data to determine the information associated with the moving object at the side of the wall different than the side of the wall of which the system is located.

Moreover, the transmission circuitry can be configured to enable the transmission of the stepped-frequency radar signal to begin at a first system location and to continue during movement of the system from the first system location to a second system location. The receiving circuitry can be configured to receive the detected reflections of the transmitted signal during the movement of the system from the first system location to the second system location. The processor can be configured to determine the information associated with the moving object located at the side of the wall different than the side of the wall of which the system is located based upon the reflections detected during the movement of the system from the first system location to the second system location. To generate the data, the receiving circuitry can be configured to generate data for detected reflections which includes information associated with frequency and phase shifts and information associated with the characteristics of the motion of the system. To analyze the generated data, the processor can be configured to generate a synthetic aperture radar image using the data including information associated with frequency and phase shifts and information associated with the one or more characteristics of the motion of the system.

In addition, the system can include an inertial sensor configured to determine the one or more characteristics of the motion of the system and to generate the data, the receiving circuitry can be configured to sample output of the inertial sensor and to generate a packet of data for reflections received at multiple system locations between the first and second system locations, each packet including the information associated with frequency and phase shifts, and output of the sampled inertial sensor at the time the reflection was detected.

The processor can be configured to identify a transmit-to-receive leakage signal resulting from the transmission of the stepped-frequency radar signal, generate a cancellation waveform configured to remove effects of the identified transmit-to-receive leakage signal, and use the generated cancellation waveform to remove effects of transmit-to-receive leakage signal of subsequent transmissions. The processor can be configured to, after the transmission of the stepped-frequency radar signal, determine the stepped-frequency radar signal should be altered, enable generation of the altered stepped-frequency radar signal such that the order of the transmitted frequencies is changed or such that one or more of the transmitted frequencies is removed, and enable the transmission circuitry to transmit the altered stepped-frequency radar signal. To use the one or more characteristics of motion of the system, the processor can be configured to use one or more characteristics of motion of the antenna.

In other implementations, some aspects include a system for detecting entities based on movement. The system includes transmission circuitry configured to enable transmission of a stepped-frequency radar signal and an antenna configured to detect reflections of the transmitted signal. The system also includes receiving circuitry configured to receive detected reflections from the antenna and to generate data including information associated with frequency and phase shifts between the transmitted signal and the reflections of the transmitted signal. The system further includes processing means to receive the generated data from the receiving circuitry and to analyze the generated data to determine information associated with a moving object located at a side of a wall different than a side of the wall of which the system is located. The analyzing includes using one or more characteristics of motion of the system to compensate for the effect of the motion of the system on the phase shifts between the transmitted signal and the reflections of the transmitted signal.

The details of one or more implementations are set forth below. Other features will be apparent from the description and drawings, and from the claims.

DESCRIPTION OF DRAWINGS

FIG. 6A is a diagram illustrating use of multi-static motion detection with a scanning device.

Like reference symbols in the various drawings indicate like elements.

DETAILED DESCRIPTION

In order to detect the presence of entities through movement when visual detection is blocked (e.g., by a wall), a device, such as a handheld scanner, includes a stepped-frequency radar transmitter. The transmitter emits a radar based signal that includes different frequencies. The emitted signal strikes objects and is partially reflected. The reflected signal may be affected by environmental characteristics (e.g., movement of an object or entity or distance to the object or entity). For example, if an object is moving closer to the device, signals reflected from the object will exhibit a frequency shift (i.e., a Doppler shift) that may be observed and processed by the device. Also, the distance a signal travels before or after being partially reflected affects the phase of the reflected signal at the receiver.

Various processing methodologies and hardware configurations can be used by the device to analyze characteristics of reflected signal for useful information. For example, processing information received from multiple receives can be used to determine a location in 2 or 3 spatial dimensions of detected movement. Also, detecting differing rates of movement may require separate processing algorithms and/or separate characteristics of the transmitted signal. For example, in one implementation, a shorter duration (e.g., a few seconds) of signal transmission at a set of frequencies may be transmitted to detect fast moving objects, such as an individual running while a longer duration (e.g., less than 10 seconds) signal transmission may be employed to detect slower moving objects, such as the chest cavity of an individual breathing.

The device may be used to aid in military or search and rescue missions. For example, soldiers may use the device to detect the presence of unknown individuals that may be hiding behind walls. A soldier may activate the device while aiming the transmitter such that the signal is pointed at a closed door. The signal may penetrate walls and doors, and partially reflect when striking an individual (e.g., an enemy soldier). The reflected portion of the signal may exhibit a frequency shift detectable by the device at multiple receivers. The device receives and processes the reflected signal from the receivers, and may determine a presence in three spatial dimensions of one or more entities. Also, the device may be used to detect the presence of individuals buried in piles of rubble based on subtle movement, such as breathing.

Figure 1A:
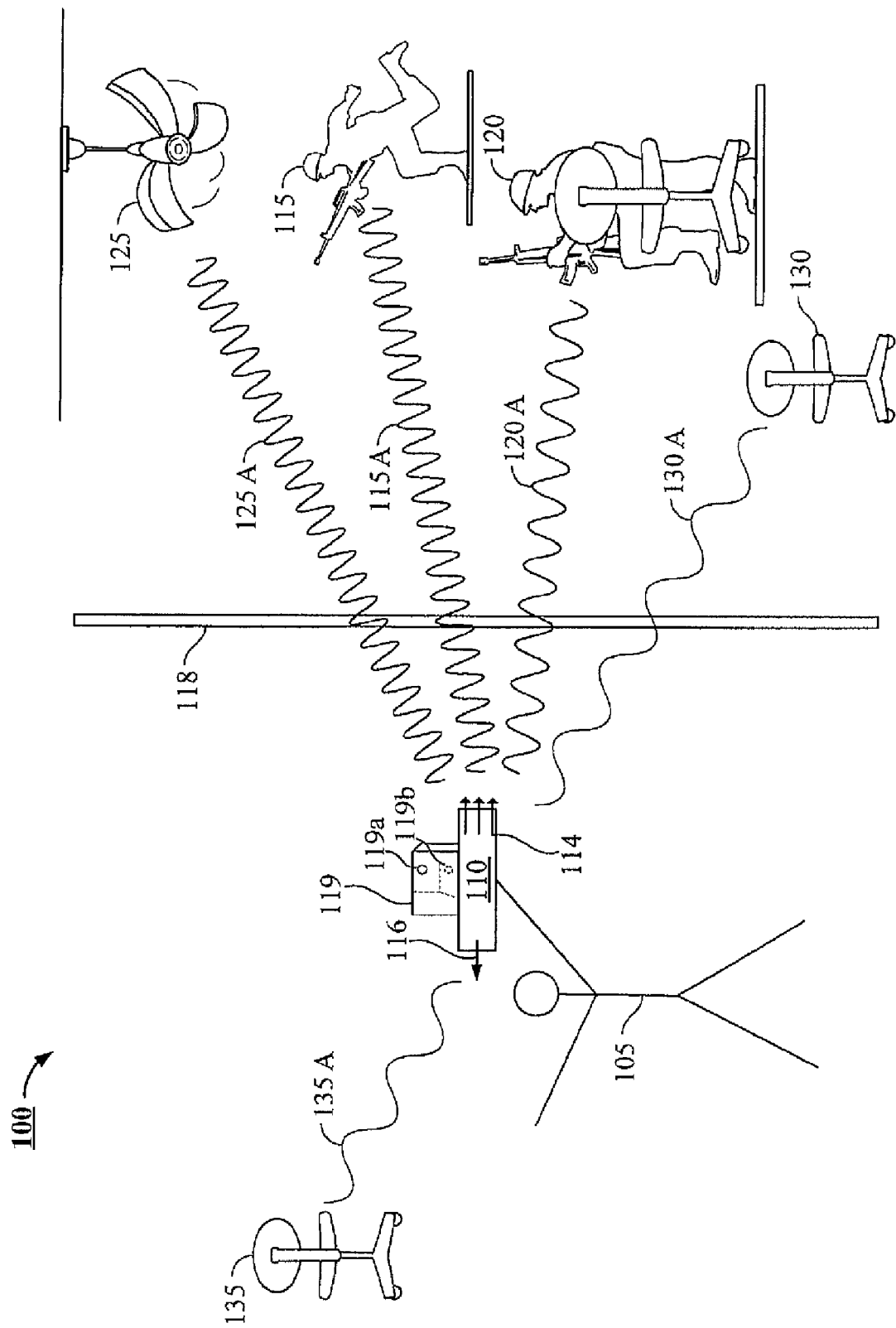
FIG. 1A is a diagram illustrating use of a scanning device for detecting moving entities.

FIG. 1A shows a diagram 100 illustrating use of a scanning device for detecting moving entities. In the diagram 100, a user 105 holds an activated handheld stepped-frequency sensor device 110, which transmits stepped-frequency radar signals.

As shown, the device 110 includes several forward looking antennas 114 and a backward looking antenna 116 (shown as arrows). This configuration is one example, various implementations of the device 110 and its arrangement of antennas are discussed in FIGS. 5A-7. Also, a single transmitted signal from the device 110 is described for simplicity, although multiple signals can be transmitted as discussed in FIGS. 6A-7. The device 110 may differentiate between signals received from the forward looking antennas 114 and those received from the backward looking antenna 116 to determine information associated with the location of detected movement (e.g., whether the movement occurs in front of or behind the device).

In the diagram 100, the device 110 has been operated to transmit a signal either with one of more of the antennas as transceivers or with a separate transmitter. The signal (not shown) propagates outwards, strikes objects, and is reflected 115A, 120A, 125A, 130A, and 135A. As received by the device 110, the reflected signal exhibits a frequency shift proportional to the magnitude of the object's movement towards or away from the device.

In particular, the signal may penetrate a wall 118 and be partially reflected by a running individual 115, a sitting individual 120, a spinning ceiling fan 125, and a stationary chair 130 on the opposite side of the wall. The signal also is partially reflected by a nearby stationary chair 135 that is on the same side of the wall 118 as the user 105. The signal 120A reflected by the sitting individual 120 exhibits a small frequency shift due to the breathing movement of the individual's chest cavity. The signal 115A reflected by the running individual 115 exhibits a larger frequency shift than the partially reflected signal 120A from the sitting individual 120, with this frequency shift being due to the more pronounced movement of the body of the running individual 115. The signal 125A reflected by the spinning ceiling fan 125 exhibits a frequency shift that is characteristic of a repeated mechanical movement. The signals 130A and 135A that are reflected by the stationary chair 130 and the nearby stationary chair 135 exhibit no frequency shift.

The device 110 receives and processes the frequency and phase information from the partially-reflected signals 115A, 120A, 125A, 130A, and 135A. The signals may be received using a single antenna or using forward and backward looking antennas. In an initial scan function, the device 110 may calibrate against data associated with partially-reflected signals that exhibit no frequency shift 130A and 135A or that exhibit only a frequency shift due to mechanically repeated movement 125. The processed data indicates movement reflective of both breathing and running. In some implementations, the device 110 provides indications of detected moving objects by lighting separate lights or providing other types of visual indicators. In other implementations, the device 110 can provide the results of the scan on a display screen 119 along with various information determined by processing.

In this example, the device uses three forward looking antennas to determine the location of objects in three spatial dimensions (as discussed in FIGS. 5A-5B) and provides a visual display of the relative location of two detected moving objects. Although reflected signal from the running individual 115, the sitting individual 120, the spinning ceiling fan 125, and the stationary chairs 130 and 135 have all indicated the existence of objects, only two are shown on the display screen 119. Using processing techniques discussed below, the device 110 has removed the fully stationary objects (e.g., the chairs 130 and 135) and the objects exhibiting characteristics of repetitious mechanical movement (e.g., spinning ceiling fan 125) from consideration. Also, processing techniques of the device 110 have determined the sitting individual 120 to be exhibiting movement indicative of a stationary person (e.g., only subtle breathing movement) and the running individual 115 to be exhibiting movement indicative of an active person. Therefore, of the detected objects, only the two individuals are represented on the display screen 119.

The significance of the movement and its location in space relative to the device are shown. Specifically, the running individual 115 is represented on the display screen with a larger, more pronounced indication 119a to signify the significant level of movement whereas the sitting individual 120 is represented on the display screen with a smaller, less pronounced indication 119b to signify the less significant movement. Other implementations may show (or include options to show) all detected objects or a subset thereof (e.g., show objects with repeated mechanical movement, show stationary objects, show any object detected that is between a detected moving object and the device 110).

Figure 1B:
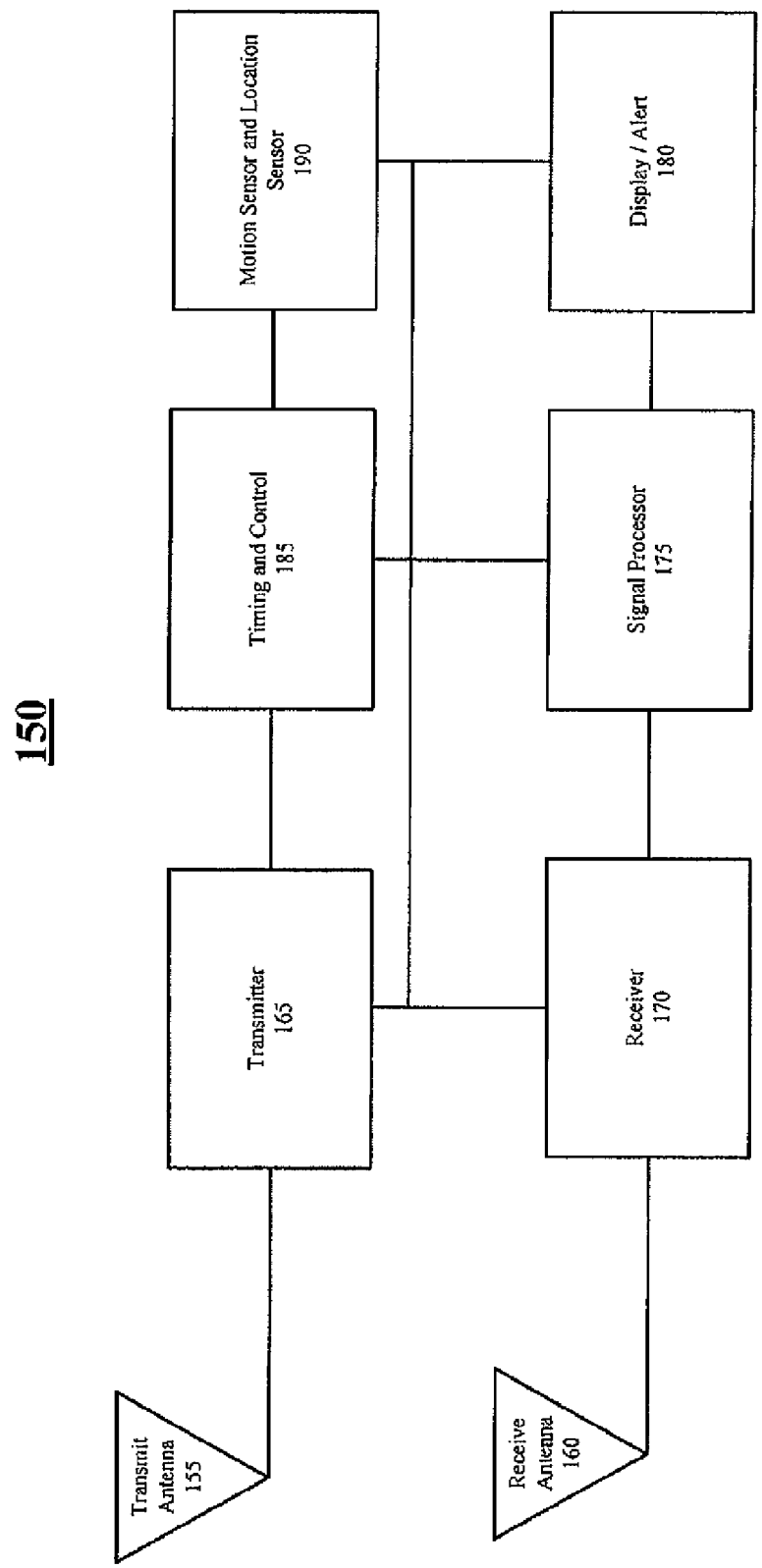
FIG. 1B is a block diagram of a stepped-frequency scanning device configured to detect moving entities.

FIG. 1B is a block diagram of a stepped-frequency scanning device 150 configured to detect moving entities. Although discussed in terms of a device, the elements can be used as a system or apparatus of commonly located or separated elements. The device 150 includes antennas 155 and 160 for transmitting and receiving a stepped-frequency radio frequency signal (an "RF signal") to detect moving entities. The device 150 is shown as a bistatic radar, in that there are separate antennas for transmitting and receiving the RF signal. In particular, a transmit antenna 155 is connected to a radar transmitter and transmits an RF signal toward a target, and a receive antenna 160 is connected to a radar receiver and receives a portion of the RF signal that is reflected by the target. In other implementations, the device 150 may be a monostatic radar that uses a single antenna as a transceiver to both transmit and receive the RF signal. Also, various implementations may use multiple transmit antennas 155 and/or multiple receiving antennas 160.

The transmit antenna 155 is connected to a radar transmitter 165 that transmits an RF signal toward a target. Implementations using more than one concurrent transmission (discussed below) may use one or more transmit antennas 155 which can be coupled to either a single shared/multiplexed radar transmitter 165 or multiple dedicated radar transmitters 165. The transmitted RF signal can include frequencies that cover a bandwidth in increments of frequency steps. For example, the signal may include a nominal frequency operating with a center frequency in the UHF, L, S or X bands.

The receive antenna 160 is connected to a radar receiver 170 and receives the reflected RF signal from the target. For simplicity, the receive antenna 160 is discussed in terms of the implementation including a single antenna. Nevertheless, the receive antenna 160 may represent two or more antennas as shown by the forward looking antennas 114 of FIG. 1A. Implementations employing multiple antennas may each have a dedicated receiver which is shared or otherwise multiplexed, or may include multiple dedicated receivers.

The receiver 170 is coupled to a signal processor 175 that processes received RF signals from the receiving antenna 160. The signal processor 175 is coupled to a display 180 and a timing and control module 185. The display 180 provides audible and/or visual information or alerts of objects detected by the device, such as those described with the display screen 119 of FIG. 1A. The timing and control module 185 may be connected to the transmitter 165, the receiver 170, the signal processor 175, and the display 180. The timing and control module provides signals, such as a clock signal and control signals, to the other components of the device 150. Implementations may employ detection processes for slow or fast movement that run in real-time on an embedded processor. Implementations also may employ interference detection processes.

The signal processor 175 can include an interferometer/interferometer processing. The interferometer can process received signal to enable location of entities or targets within a given environment. The interferometer also can provide simultaneous stationary object mapping capability. In particular, the interferometer may receive channel signals, use a low-pass filtered to provide stationary object mapping, and use a high-pass filter for moving target angle estimation.

The device 150 also includes a motion sensor 190 which may include an internal inertial sensor and/or global positioning system (GPS) sensor or other location sensors. Detection of moving and/or breathing targets during handheld and/or on-the-move operation of the device 150 is supported through use of the motion sensor's measurement and resulting compensation during processing. In various implementations, an inertial measurement sensor, with or without the use of a global positioning sensor, can be incorporated with the motion sensor 190 to provide sensor motion measurement, thereby supporting motion compensation processing to factor out device 150 motion (as discussed below). Alternatively, or in conjunction, adaptive processing of the radar return can be used by the motion sensor 190 and/or the signal processor 175 to estimate the sensor motion independent of measurements by the motions sensor 190. Such adaptive processing can be employed by using the phase change of stationary scattering present in the scene to estimate the sensor motion.

Figure 2A:
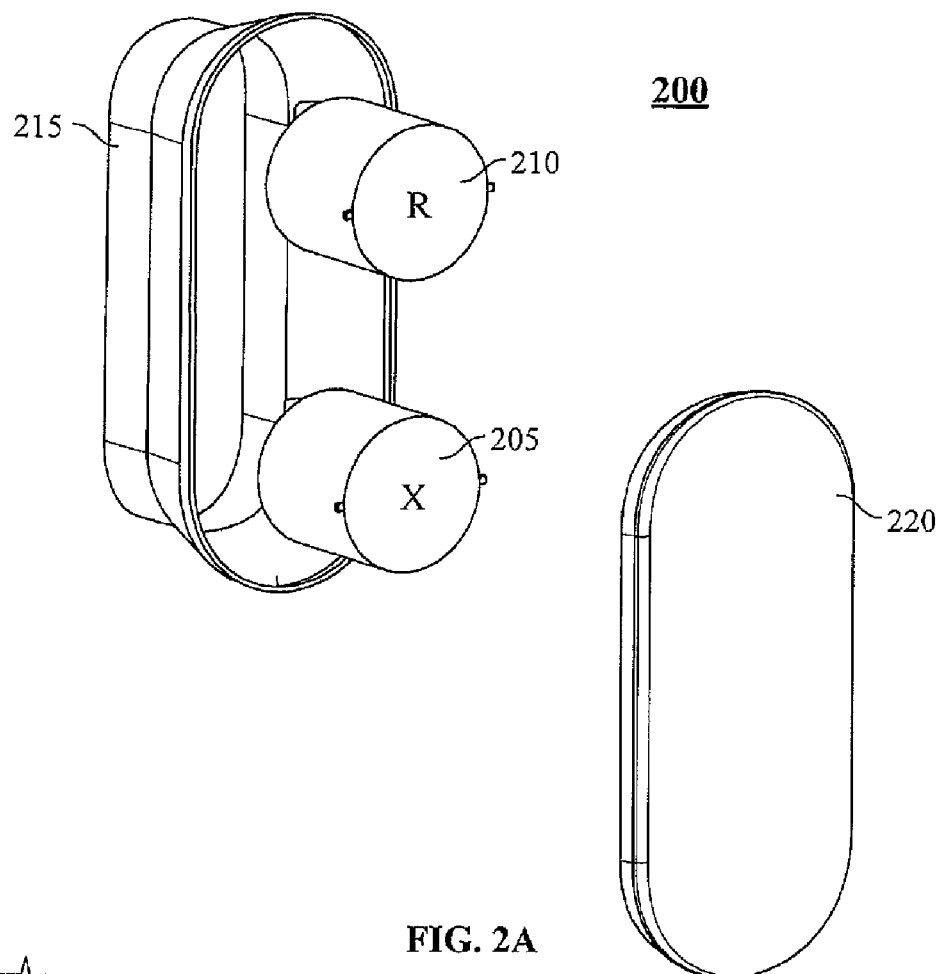
FIGS. 2A and 2B are perspective views of an antenna design for the device of FIG. 1B.

FIG. 2A illustrates an antenna design 200 employed in one implementation of the device of FIG. 1B. The design 200 employs separate transmit and receive antennas 205 and 210 to simplify the electronics, provide spatial separation and reduce very shallow reflections. The antennas 205 and 210, which may serve as particular implementations of the antennas 114 and 116 of FIG. 1B, may be placed in a housing 215, and a cover 220 may be placed over the antennas. The cover 220 may be made of a suitable radome material.

Figure 2B:
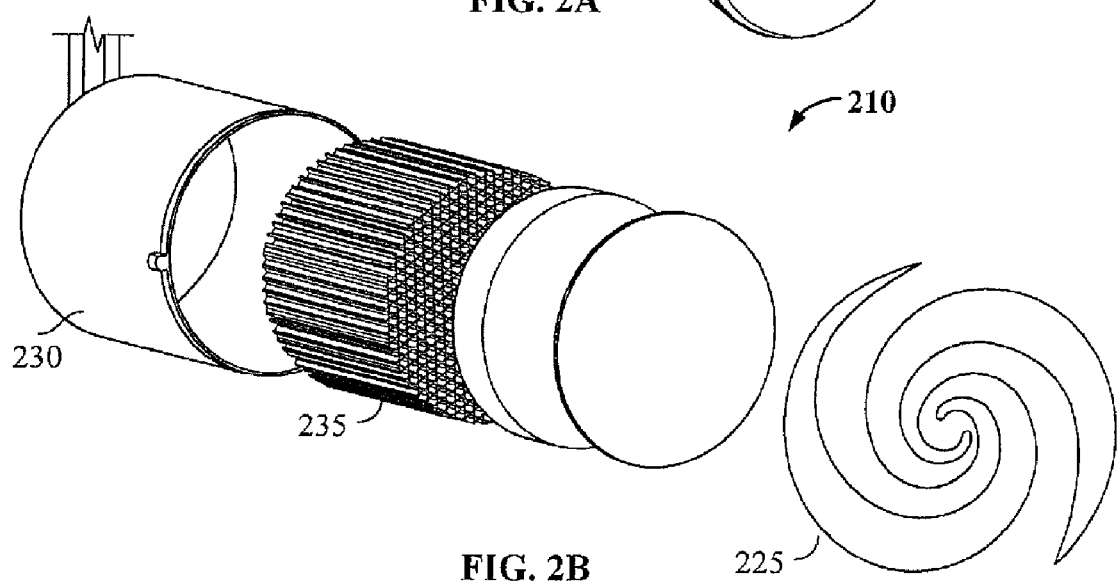

FIG. 2B further illustrates aspects of the design 200 discussed above with respect to FIG. 2A. Although the following discussion refers to the receive antenna 210, it is equally applicable to transmit antenna 205 or other antennas. As shown, the design 200 employs a spiral antenna as the receive antenna 210 to permit significant size reduction. For an antenna to be an efficient radiator, it must normally have a dimension of at least one-half wavelength. The spiral radiates efficiently when it has an outer circumference of at least one wavelength. This means that the antenna needs a maximum diameter of about one-third wavelength. The upper frequency limit for efficient spiral radiation is set by the size of the feed point attachments, and the lower frequency limit is set by the outer diameter of the spiral structure. Within these limits, the spiral radiates efficiently in a frequency-independent manner. The input impedance and the radiation patterns may vary little over this frequency range.

The receive antenna 210 may be constructed by etching a spiral pattern on a printed circuit board. A planar, printed circuit, spiral antenna radiates perpendicularly to the plane of the spiral. The spiral 225 itself is located at the end of a cylindrical metal cavity 230 (the cavity back) to provide isolation from neighboring elements and electronics. Typically, an absorber 235 is used on the back side of the spiral inside the cavity 230 to make sure the element responds only forward.

The previous description provides an example implementation of an antenna design. Other implementations may include different antennas, such as an endfire waveguide antenna. Such a configuration may be slightly larger than the spiral configuration. The endfire waveguide antenna reduces the measurement spot size, thus making a more precise position of a concealed object easier to locate. Other suitable types of wideband antennas may also be used.

Figure 3:
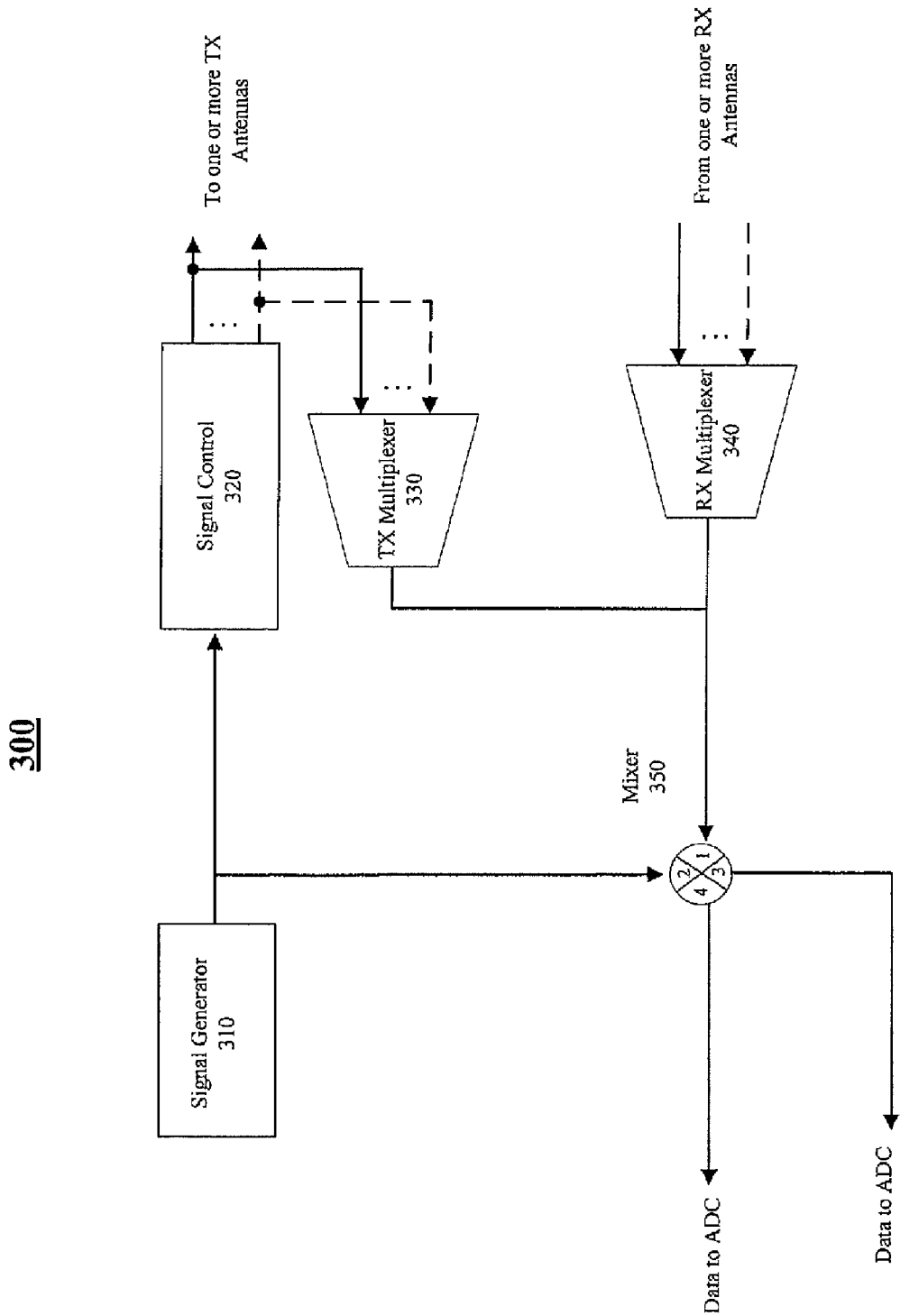
FIG. 3 is a diagram of an example conversion circuit in a scanning device.

FIG. 3 is a diagram of an example conversion circuit 300 in a scanning device. The circuit 300 can be used as portions of the transmitter 165 and receiver 170 of FIG. 1B. Also, the circuit 300 includes a signal generator 310, a signal control 320, a transmission multiplexer 330, a receive multiplexer 340, and a mixer 350, which may be in the form of a quadrature demodulator. In the circuit 300, one or more transmission signals are generated and transmitted through one or more transmit antennas. Reflected portions of the transmitted signal are received through one or more receive antennas, which may optionally be the same antennas as the one or more transmit antennas. The received signal and the signal generated by the signal generator 310 are input to the mixer 350, which outputs an in-phase signal and an out-of-phase (quadrature) signal.

Specifically, the signal generator 310 generates a signal to be transmitted by the one or more transmit antennas. The signal generator 310 may include a phase lock loop synchronized by an oscillator. In one implementation, a temperature controlled crystal oscillator is used to synchronize a voltage controlled oscillator. The signal generated by the signal generator 310 may be input to a mixer 350 and to a signal control 320. The signal control 320 may amplify or otherwise condition the signal to enable transmission by the one or more transmit antennas. The signal control 320 inputs the signal to the one or more transmit antennas and to a transmission multiplexer 330. The signal control 320 includes one or more signal outputs, each dedicated to one of the one or more transmit antennas and coupled to the transmission multiplexer 330. The transmission multiplexer 330 enables sequential sampling of the one or more signal outputs of the signal control 320 to provide feedback of the transmission signal to the mixer 350. The transmission multiplexer 330 may function as a single pole double throw (SPDT) switch for each of the signal outputs of the signal control 320.

The one or more transmit antennas emit the transmission signal, which encounters objects in the environment. Portions of the transmission signal may be reflected. The reflected portions, which may exhibit a frequency and phase shift, are received by the one or more receive antennas. Each receive antenna inputs received signal to a receive multiplexer 340. The receive multiplexer 340 enables sequential sampling, by the mixer 350, of the signal received by each of the one or more receive antennas. The receive multiplexer 340 may function as a SPDT switch for each of the signals received by the one or more receive antennas.

Some implementations may use other mechanisms, such as a control system, in place of the transmission multiplexer 330 and the receive multiplexer 340. In one implementation, the one or more receive antennas are input directly to a mixer without a multiplexer.

The mixer 350 receives the signal from the signal generator 310 at a first input. Based on the transmission multiplexer 330 and the receive multiplexer 340, either the transmission signal or the received signal is provided to the mixer 350 at a second input. The mixer 350 converts input signals to a form that is more easily processed, such as, for example, an in-phase and an out of phase component at a baseband frequency. As shown, the mixer 350 is a quadrature demodulator, though other signal conversion systems may be used. The quadrature demodulator outputs "I" and "Q" data (referred to as IQ data) which can be sent to an analog-to-digital (A/D) converter. In some implementations, separate IQ data may be generated for each transmitted frequency.

The previous description is an example implementation of the transmit and receive circuit. Other implementations may include different components. For example, in various implementations, a single transmit antenna and a single receive antenna are each coupled to a switch rather than the transmission multiplexer 330 and the receive multiplexer 340.

Figure 4A:
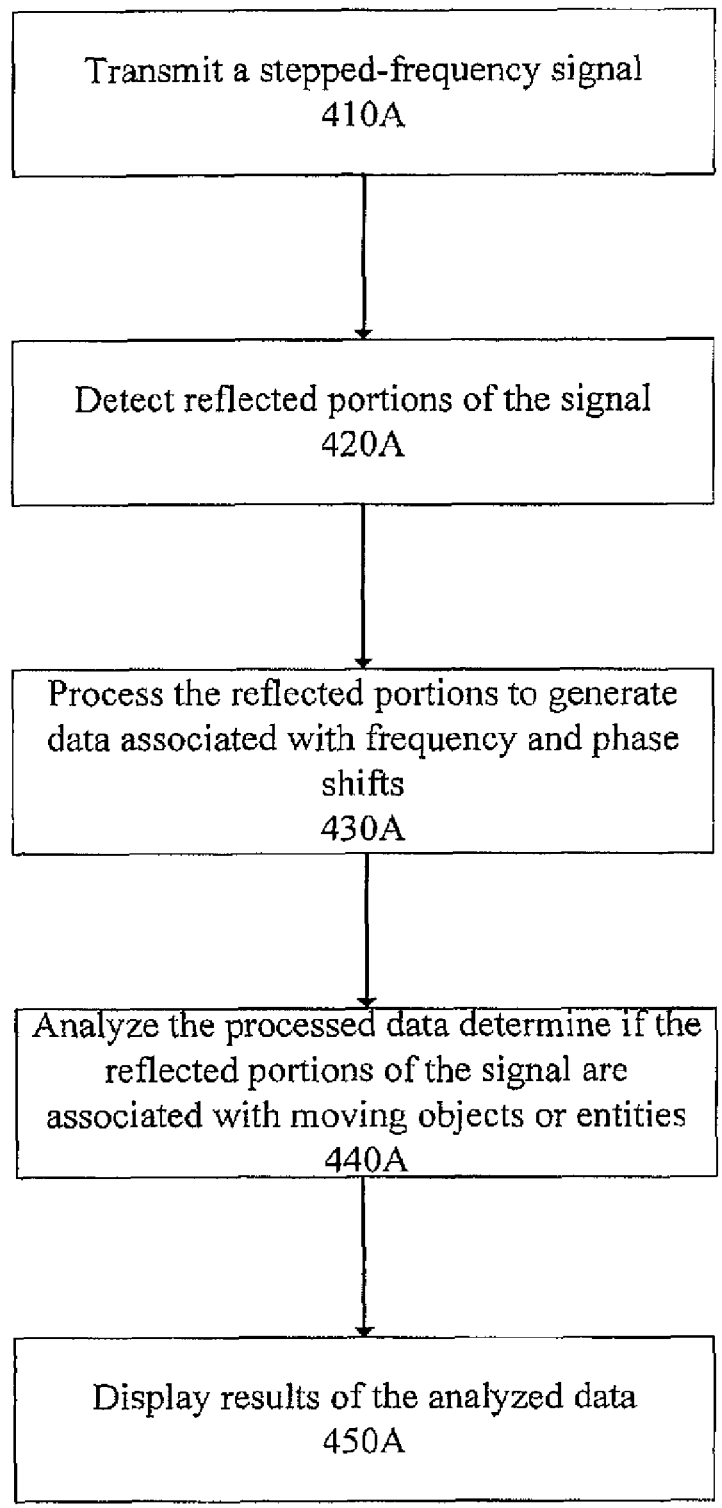
FIG. 4A is a flow chart of an example of a process to detect moving entities using a transmitted stepped-frequency signal with a scanning device.

FIG. 4A is a flow chart of an example of a process 400A to detect moving entities using a transmitted stepped-frequency signal with a scanning device. The process 400A may be implemented with the device 150 of FIG. 1B or with other devices. Also, the process 400A may be implemented in conjunction with the processes of Figs. described below.

The process 400A begins when a stepped-frequency signal is transmitted by a device (410A). The stepped-frequency signal may be an RF radar signal including multiple frequencies and phases that are transmitted concurrently or consecutively. In one implementation, each transmission includes cycling through a frequency band such that multiple frequencies are transmitted. Specifically, while cycling through the band, each frequency is transmitted for a period of time, followed by the next frequency, until the bandwidth has been crossed. Although multiple frequencies may be sent, one after another, the transmitted and received signals are discussed here and elsewhere as a single signal to simplify discussion. After transmission, the signal strikes an object and is partially reflected.

Some implementations use multiple concurrent transmission for multi-static motion detection. Specifically, the multiple transmissions of the stepped frequency signal (410) may include use of multiple transmit antennas simultaneously to form a multi-static radar. The transmit antennas may be located on a single device or across multiple devices. The combined measurements of signals can be received from the multiple transmissions by one or more receivers and can be used in processing to reduce interference and enhance detection of movement or location thereof. In some implementations, the transmit frequencies of the antennas are made different to avoid mutual transmission-interference. Also, the antennas can be networked (on a single device or between multiple devices) such that their transmit times are coordinated and the subsequent pre-processed data from each antenna can be processed in a central location. For implementations using multiple devices, the distances between antennas can be determined through static location survey or by using position measurement sensors.

Also, randomized frequency ordering and wide bandwidth of the transmissions may be utilized to disguise the coherent nature or minimize the effects of intentional or incidental jamming. For example, various implementations utilize a stepped-frequency pulse in which certain pulse frequencies are omitted in processing to screen out radio frequency interference from surrounding incidental or intentional sources. Also, a non-uniformly spaced, monotonically ordered, stepped-frequency waveform may be used. Further, a non-monotonically ordered stepped-frequency waveform or a frequency-hopped tonal waveform also may be used. The transmitted waveform frequency steps can be transmitted in an order dictated by a quadratic congruential sequence. Two or more antennas can be operated simultaneously using mutually orthogonal stepped-frequency transmit sequences, such as, for example Bellegardia Sequences or Quadratic Congruences.

In addition, some implementations enhance the effective aperture of the radar by moving the transmitting antenna along a pre-determined or motion-sensed line segment using a synthetic aperture radar (SAR) imaging operation mode. In particular, the stepped-frequency signal is transmitted by the device (410A) while the device is linearly moved. The known movement is combined with the received reflections and taken into account during processing to form a SAR image. During such operation, information provided by a device's inertial measurement and/or location sensors can be used to assist the user in providing a proper motion or by the processor in correcting for imperfections in the motion.

The device detects the reflected portion of the signal (420A). This detection can be accomplished using a transceiver, a separate antenna, or multiple separate antennas (e.g., a forward looking and backward looking antennas or multiple forward looking antennas). In one implementation, a single transceiver transmits the stepped-frequency signal and receives reflected portions therefrom. The detected signal includes a frequency that may have been altered by movement of the struck object and a phase that may be affected by the distance to the object.

Other implementation use multiple antennas for detection to enable more specific determination as to the location of an object (or entity). Using multiple antennas spaced at known distances and positioned to receive signals in a similar direction can enable a more accurate two or three dimensional identification of an entity. In particular, processing the measurements from two or more antennas, separated in a horizontal direction may be conducted to provide an estimate of azimuth angle-of-arrival. Moreover, elevation angle-of-arrival estimation may be provided by processing measurements from two or more antennas that are separated in a vertical direction. Simultaneous azimuth and elevation interferometry can enable estimation of each target's location in three spatial dimensions. The device's existing receiver can be multiplexed between multiple receiving antennas and/or additional receivers can be added to the device to receive the signals from multiple antennas simultaneously.

The device processes the reflected portions of the signal to generate data associated with frequency and phase shifts (430A). The processing, for example, may identify information associated with frequency and phase shifts that may be indicative of the presence of moving objects or objects at a distance. The processing may include a calibration step to calibrate the data or processing steps based on conditions detected for a particular use of the device. Calibration may include removing or altering parts of the signal indicative of clutter, repeated mechanical movement, signal leakage, or reflections near or behind the device. Processing may also include calibration of the analysis steps, such as integration time.

To improve stationary object mapping and to reduce the subsequent dynamic range of the received signal data, leakage cancellation can be used in the calibration processing. Specifically, various components of the transmit-to-receive leakage signal can be adaptively located and removed from the received signal. Such components can generally be orders of magnitude higher than the highest reflected signal. Their cancellation can provide a reduced dynamic range of the subsequent signal data, and also can suppress the range sidelobes of the leakage signal which otherwise may obscure lower amplitude stationary targets.

In some implementations, the device uses a motion and/or location sensor to calibrate information from the reflected portions of the signal during or prior to processing. Specifically, motion or location information can be used to support motion compensation processing to factor out device motion. Also, adaptive processing of the radar return can be used by the device to estimate device motion. Such adaptive processing can be employed by using the phase change of stationary scattering present in the scene to estimate the sensor motion.

The device analyzes the data to determine if the reflected portions of the signal are associated with moving objects or entities (440A). The analysis of the data (440A) may include use of a short-time Fourier Transform to estimate the Doppler shift of the return signals as one of multiple Fourier Transformation integration times. In particular, the analysis may include using a low-pass filter to provide data for stationary object mapping and using a high-pass filter to provide data for moving target angle estimation. In various implementations, other techniques may be used to accomplish this estimation. In particular, processing techniques such as Maximum Likelihood Method, Maximum Entropy Method, or Music Method, may offer greater resolution for micro-Doppler detection using shorter observation times. Such methods can be used as parametric techniques to hypothesize a particular (often autoregressive) parametric signal model enabling greater resolution in the Doppler domain with shorter observation times.

Similarly methods such as Singular Spectrum Analysis (SSA) and Higher-order statistics based techniques (e.g., Bispectral Analysis) can also be used to better resolve very closely spaced independent target returns than is possible with direct Fourier methods. These methods can be considered in a tradeoff between greater computational cost than Fast Fourier Transform (FFT) methods versus improved resolution under certain circumstances. Moreover, other methods that focus on reducing the computational cost relative to the FFT methods can be used to create the frequency (Doppler) spectrum, such as, Discrete Cosine Transform, Fast Hartley Transform, and Walsh-Hadamard Transform. These methods may employ simpler basis functions for the orthogonal decomposition than the more complex exponentials in the FFT methods. Each of the above described processing techniques can be used in the analysis of the data (440A) and may be chosen depending on the specifics of the target application and desired specialization for optimizing implementation cost versus needed detection resolution and sensitivity.

The process 400A can configure the transmitted waveform internal structure, bandwidth extent, and duration to better match and reveal certain target characteristics and fine-grained structure. For example, the detection and identification of small movements of machinery (e.g., clock mechanisms, slow speed rotating pumps) or human motions (e.g., voluntary and involuntary facial movements and life sign processes such as breathing, heart beat and blood flow within the arterial cavities) can be targeted by the analysis of the data (440A). These targets, when re-examined with the properly designed transmitted waveform, can reveal their nature in the form of very small displacements over time that impart micro-Doppler structure on the returned signals. For example, in various implementations, movement of 50-70 microns and less can be detected through adjustments to the transmit waveform characteristics and receiver processing algorithm parameters.

Results of the analyzed data are then displayed (450A). In some implementations, the results can be displayed using a series of indicators or lights. For example, movement detected as significant (e.g., from a running individual) can result in activation of a first light while movement detected as less significant (e.g., from an individual sitting and breathing) can result in activation of a second light. In other implementations, a display screen is used to illustrate two or three dimension positions of movement with or without additional information about the movement. For example, a visual display of the relative location of multiple detected moving objects can be shown as locations on a three dimensional graph or representation of a space. The significance or level of movement of the detected moving objects can be indicated by, for example, size, shape, color, or animation of the indications. Additionally, the device can derive information of the area using information from the received reflections (e.g., derive existence of stationary objects such as walls) or by loading preexisting data (e.g., load a geographical map of an area or representation of the outlay of a building) and can populate the indications of detected movement upon the derived or loaded information.

Other information can be shown using the display screen. For example, in some implementations, the device is configured to determine the relative positions of other devices. For example, the device can locate other devices by detecting a unique broadcast signature during transmission (e.g., a particular sequence of frequency steps) or by wireless network communications. Also, individuals without a scanner may include other RF identification tags that can be similarly located and identified. The device can display the position of other located devices/individuals on the display screen by rendering a unique indication. For example, such located other devices/individuals can be displayed with a first color indication while identified unknown moving objects can be displayed with a second color indication. This can enable a unit of soldiers to, for example, identify whether a target in another room is likely a non-threat (e.g., a "friendly") or a threat (e.g., a "hostile").

Also, devices can be configured to share results of analysis with other nearby devices using wireless communication. From this shared information, the device can display results computed from other devices. For example, if a first device determines there is a moving object 3 meters in front of it that is likely a non-threat it can transmit this determination to a second device. The second device receives this information and determines the location of the non-threatening object. For example, the second device may first determine that the first device is located, for example, 4 meters left of the device. Thereafter, the second device determines that the non-threatening object is 5 meters diagonally front and left of the device based on the first device's relative location to the second device and the non-threatening object's relative location to the first device, and renders an appropriate indication on the display screen.

The process 400A is an example implementation of a process to sense moving entities using, for example, a stepped-frequency scanning device. Some implementations may include additional or alternative steps. For example, processing and analyzing the data (430A and 440A) may be conducted together.

Figure 4B:
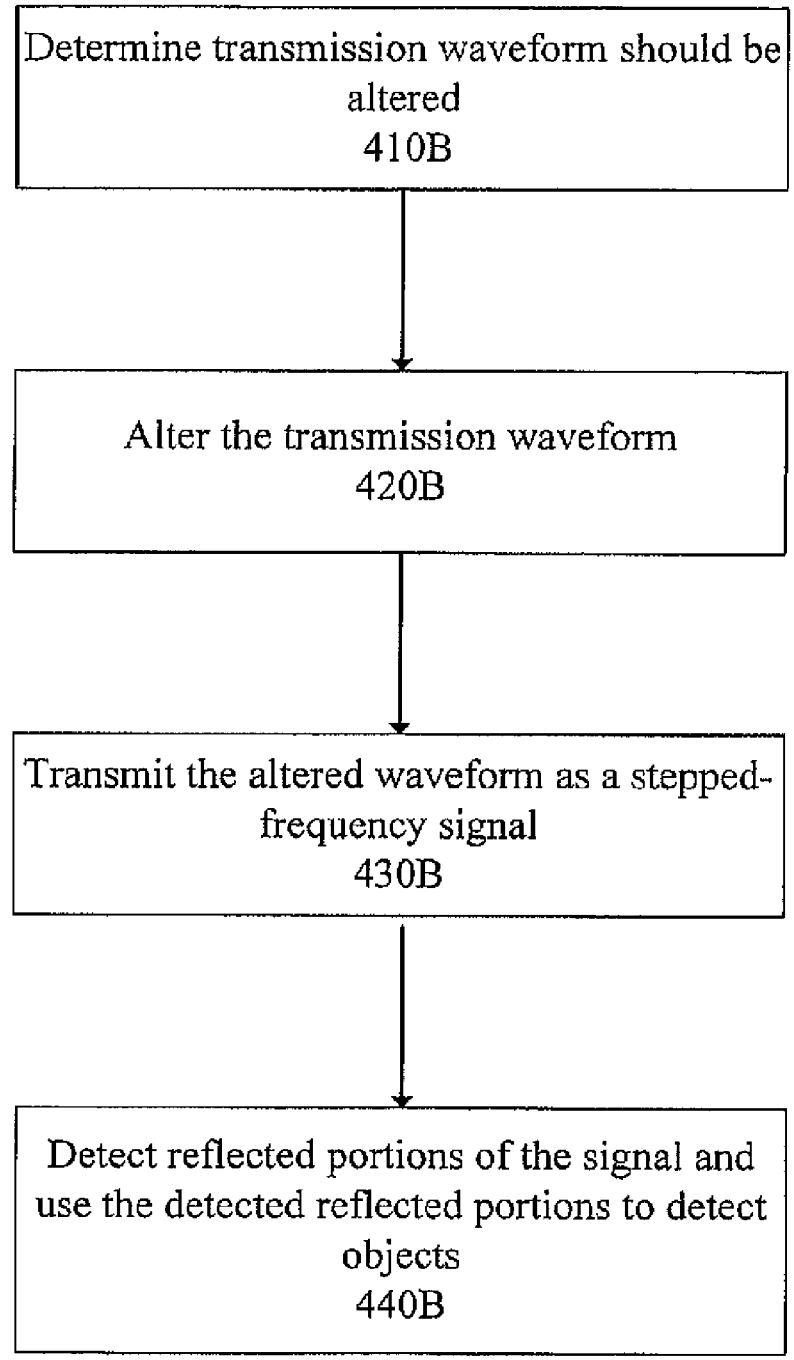
FIG. 4B is a flow chart of an example of a process to detect moving entities including altering transmitted waveforms used by a scanning device.

FIG. 4B is a flow chart of an example of a process 400B to detect moving entities including altering transmitted waveforms used by a scanning device. The process 400B may be implemented with the device 150 of FIG. 1B or other devices. The process 400B can be used along with or separate from the process 400A of FIG. 4A. By altering the transmitted waveform, a device may be able to compensate for the effects of noise or interference, and may be able to avoid or overcome the presence of signal jamming.

Initially, it is determined that the transmission waveform should be altered (410B). The determination may be made by a user or by the device. For example, in one implementation, the device includes an input option to randomize the waveform frequencies or to select alternative frequency stepping. In particular, if a previous scan yields poor results (e.g., the results seem incorrect to the user, such as excessive detections), the user can activate a manual alteration input (e.g., a button on the device). In response, the device is triggered to adjust the transmission waveform used in subsequent transmission. Also, a user may determine that alteration is needed prior to any transmission, such as, if the user suspects that an identifiable transmission may result in directed jamming. By using a manual alteration input to preemptively randomize the transmitted waveform, the coherent nature and wide bandwidth of the subsequent transmissions can be disguised or minimized, possibly preventing detection or jamming.

In various implementations, the device is configured to determine that the transmission waveform should be altered (410B) without additional user input as a result of various conditions. For example, the device can be configured to trigger alteration of the transmission waveform in response to a determination of poor results during processing and analysis of data, such as, if saturation or degraded performance is detected (discussed below). In addition, the device can be configured to determine that the transmission waveform should be altered (410B) in response to a determination that frequencies are jammed or otherwise have high levels of interference. In one implementation, the device detects signals present prior to transmission (prior to each transmission or during device power on). If a frequency is found to be unavailable due to jamming or interference, the device alters the waveform to remove frequency steps in or near the unavailable frequency.

The device proceeds to alter the transmission waveform (420B). The altering may include removing specific frequencies, changing the step pattern of the frequency steps, randomizing frequency steps, or otherwise generating a non-uniformly spaced, monotonically ordered stepped-frequency waveform. The altering may include accessing a stored transmission waveform of a series of discrete stepped-frequencies for transmission, altering one or more of the discrete stepped-frequencies or order thereof, and storing the altered transmission waveform in permanent or temporary storage (e.g., random access memory) for use during subsequent transmission.

Thereafter, the altered waveform is transmitted by the device as a stepped-frequency signal (430B). The frequency steps of the altered waveform can be transmitted in an order dictated by a quadratic congruential sequence. Also, in some implementations, two or more transmit antennas can be operated simultaneously using mutually orthogonal stepped-frequency transmit sequences, such as, for example Bellegardia Sequences or Quadratic Congruences. Reflected portions of the signal are detected and used to detect objects (440B). Multiple receiving antennas can be used. The reflected portions of the signal can be processed to generate data associated with frequency and phase shifts, analyzed, and used to display results using, for example, the techniques described above with respect to elements 430A-450A of FIG. 4A.

Figure 5A:
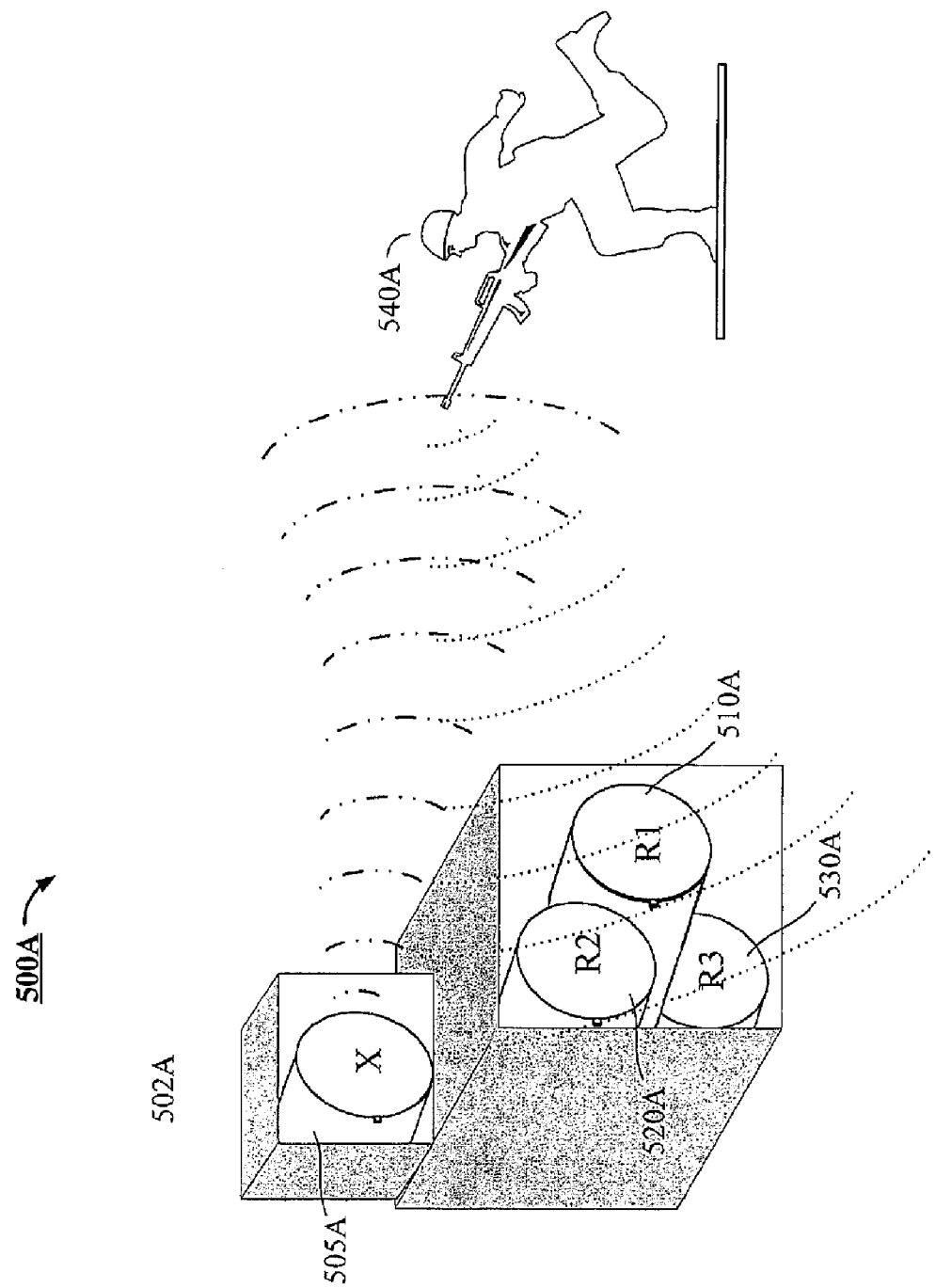
FIG. 5A is a diagram illustrating use of interferometric measurement with a scanning device.
Figure 5B:
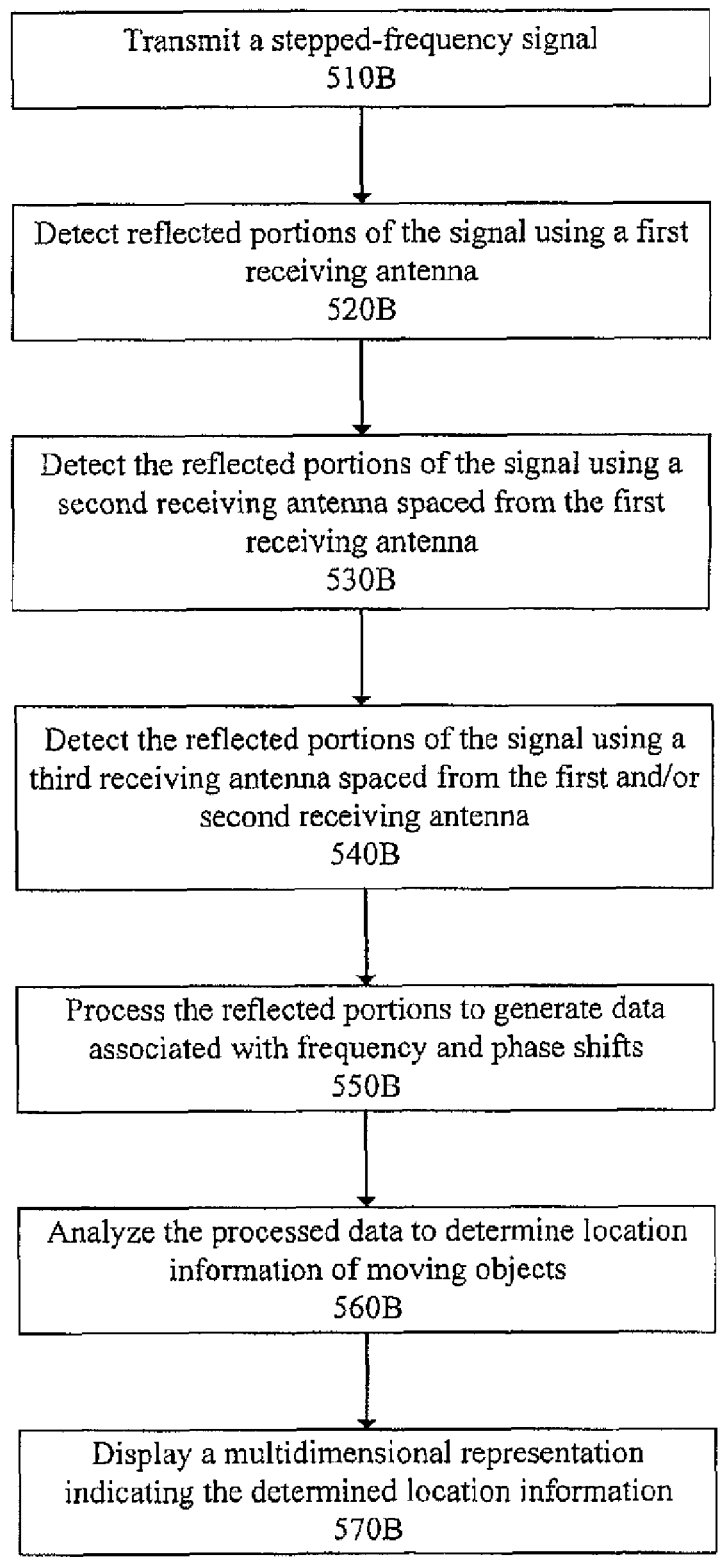
FIG. 5B is a flow chart of an example of a process to detect moving entities using interferometric measurement with a scanning device.

FIG. 5A is a diagram 500A illustrating use of interferometric measurement with a scanning device 502A and FIG. 5B is a flow chart of an example of a process 500B to detect moving entities using interferometric measurement with the device 502A. The description of FIGS. 5A and 5B is directed to the use of multiple receiving antennas. By using multiple receiving antennas, the determined location of moving objects can be of greater specificity. For example, while a single receiving antenna generally enables determination of a linear distance between the device 502A and the object, using three receiving antennas can enable determination of a location in three spatial dimensions relative to the device 502A. The device 502A may be implemented as a part of the device 150 of FIG. 1B or other devices. The process 500B can be used along with or separate from the process 400A of FIG. 4A.

Initially, the device 502A transmits a stepped-frequency signal (510B). The signal may be a stepped-frequency signal transmitted using a single transmit antenna 505A. The signal propagates outward from the device 502A and reaches a moving object 540A, where it is partially reflected. The reflected portions of the signal propagate back to the device 502A with a frequency change proportional to the magnitude with which the moving object was moving towards or away from the device 502A. As the reflected portions of the signal propagate, the phase changes with position while frequency remains constant. The reflected portions of the signal propagate past each of the first, second, and third receiving antennas 510A-530A.

The reflected portions of the signal are detected by the first receiving antenna 510A of the device 502A (520B). The first receiving antenna 510A is at a first location, and the reflected portions of the signal exhibit a first phase relative to the first location. The reflected portions of the signal are also detected by the second receiving antenna 520A of the device 502A (530B). The second receiving antenna 520A is at a second location which is spaced from the first location. The reflected portions of the signal are further detected by the third receiving antenna 530A of the device 502A (540B). The third receiving antenna 530A is at a third location which is spaced from the first and/or second locations.

In one implementation, the first and second receiving antennas 510A and 520A are separated along a first axis (e.g., horizontally) to create a first interferometric pair and the third receiving antenna 530A is separated from the first and/or second receiving antennas 510A and 520A along a second axis which is perpendicular to the first axis (e.g., vertically) to create a second interferometric pair. In addition, the back lobe of a rear facing antenna (not shown) can be used in conjunction with the first and second interferometric pairs which are forward looking in the diagram 500A to provide additional interferometric measurement capability to increase accuracy of angle of arrival estimation. Different implementations can place the receiving antennas 510A-530A differently, such that they are separated by multiple dimensions. Although discussed as three separate occurrences for simplicity, the detections (520B-540B) can be conducted nearly simultaneously (i.e., detection can be temporally separated only by the time of propagation by the reflected signal).

The reflected portions are processed to generate data associated with frequency and phase shifts (550B) using, for example, the techniques described above with respect to element 430A of FIG. 4A. The processed data is analyzed to determine location information of moving objects (560B). In the analysis, the spatial locations of the receiving antennas 510A-530A and the phase of the reflected portions as measured by the receiving antennas 510A-530A are taken into account to determine the physical position of the moving object 540A relative to the device 502A.

In particular, the device 502A uses the phase differences between reflected portions of the signal as received by the first and second receiving antennas 510A and 520A and the known physical locations of the first and second receiving antennas 510A and 520A (e.g., in this implementation, separated horizontally) to determine the azimuth angle-of-arrival of the reflected portions of the signal. Also, the device 502A processes the phase differences between reflected portions of the signal as received by the second and third receiving antennas 520A and 530A and the known physical locations of the second and third receiving antennas 520A and 530A (e.g., in this implementation, separated vertically) to determine the elevation angle-of-arrival. The device 502A uses azimuth and elevation interferometry of the data to determine the physical location of the moving object 540A in three spatial dimensions.

Finally, the device 502A displays a multidimensional representation indicating the determined location information of the moving object 540A (570B) using, for example, the techniques described above with respect to element 450A of FIG. 4A.

Figure 6B:
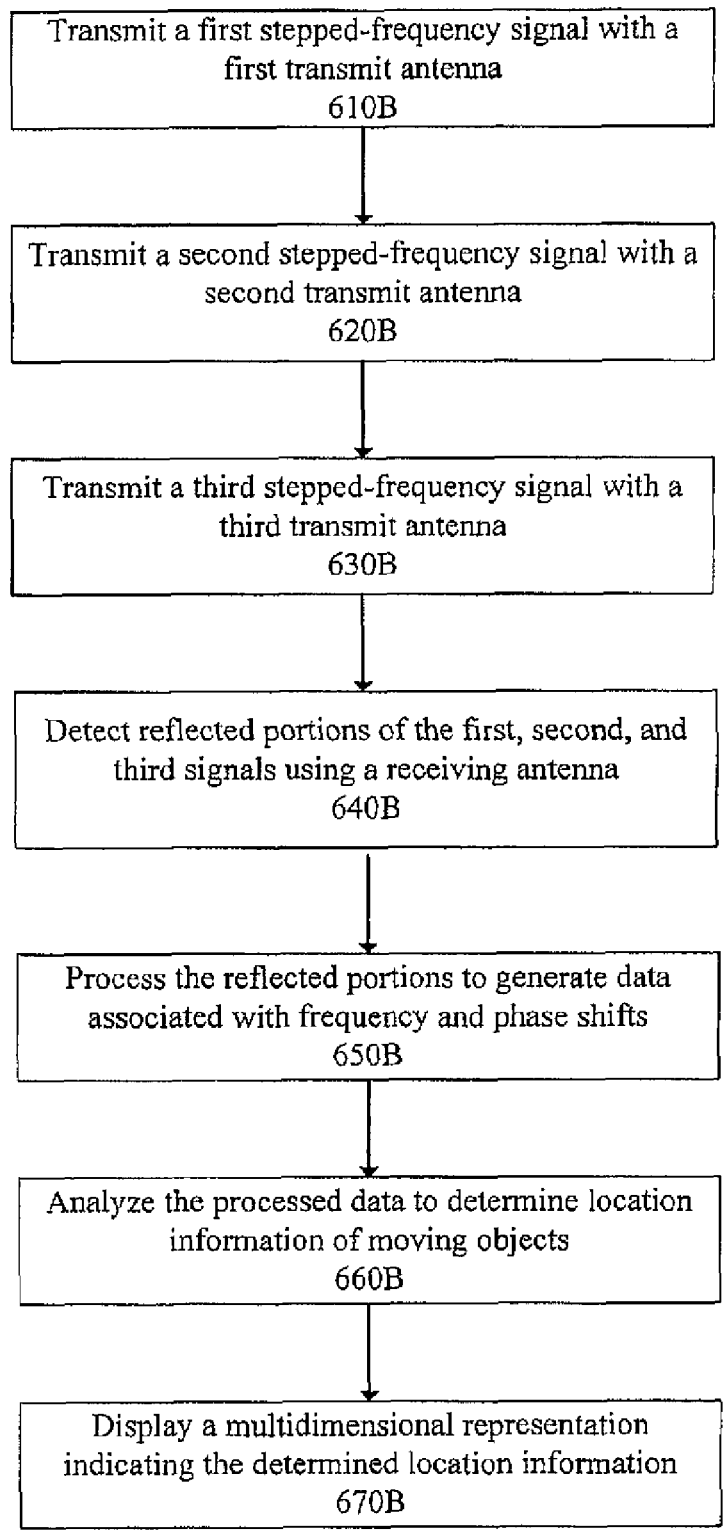
FIG. 6B is a flow chart of an example of a process to detect moving entities using multi-static motion detection with a scanning device.

FIG. 6A is a diagram 600A illustrating use of multi-static motion detection with a scanning device 602A and FIG. 6B is a flow chart of an example of a process 600B to detect moving entities using multi-static motion detection with the device 602A. The description of FIGS. 6A and 6B is directed to the use of multiple signal transmissions. By using multiple transmissions, more precise identification of movement and location thereof can be provided. Moreover, the multiple transmissions can protect against degraded results due to jamming, interference, or noise. Additionally, some implementations conduct the transmissions in a sequence to enable faster refreshing of a display screen. The device 602A may be implemented as a part of the device 150 of FIG. 1B or other devices. The process 600B can be used along with or separate from the process 400A of FIG. 4A.

Figure 7:
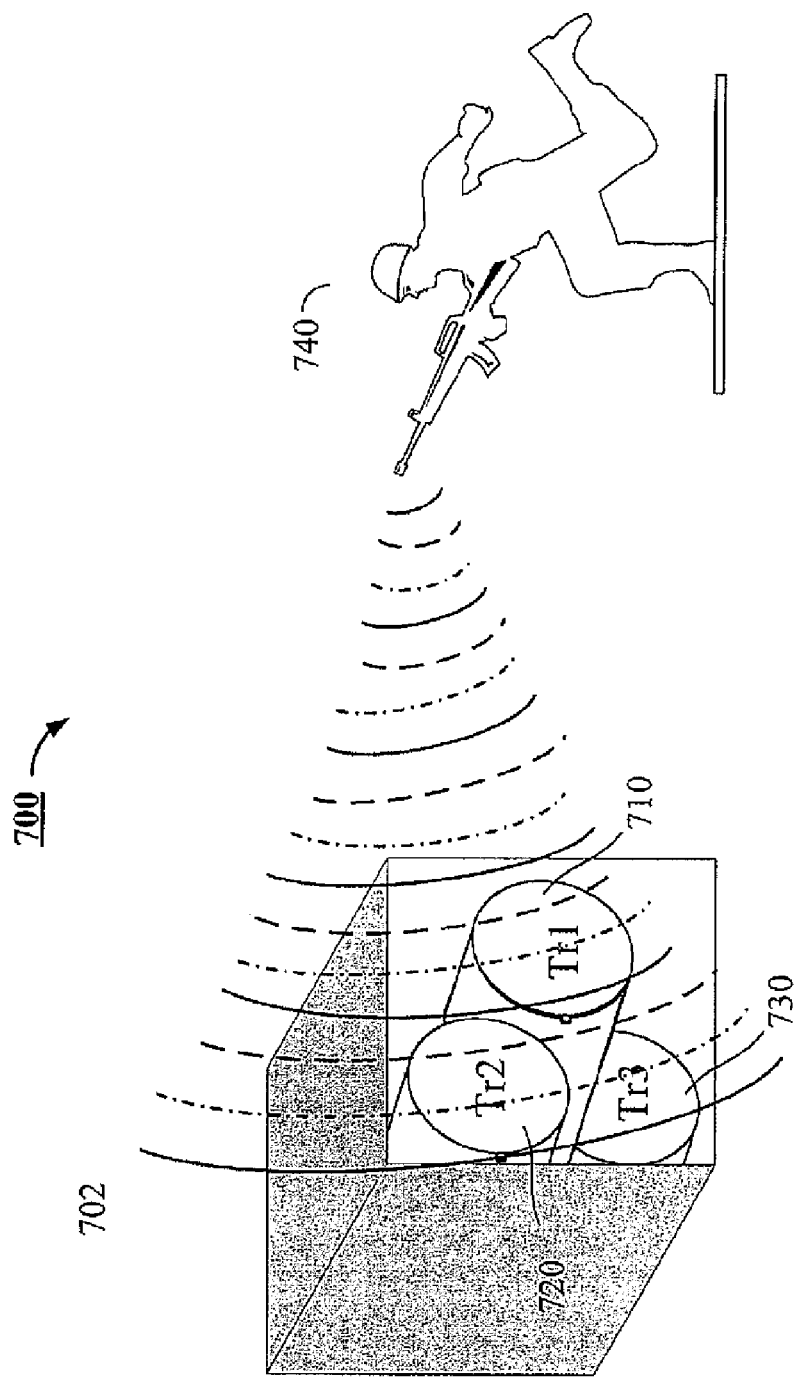
FIG. 7 is a diagram illustrating use of transceivers to conduct interferometric measurement and multi-static motion detection with a scanning device.

As shown in the diagram 600A, the three transmit antennas 610A-630A are part of a single device 602A. In one implementation, the transmissions occur on a single shared transmit antenna (not shown) to minimize device size and required components. The use of dedicated transmit antennas, however, can reduce circuit complexity and lower issues of interference. Moreover, for implementations employing interferometric measurement and the use of transceivers as shown in FIG. 7, separate antennas may be needed for receipt of signals, and therefore may be utilized for separate transmission as well.

Initially, first, second, third transmit antennas 610A-630A are used to transmit three signals. Specifically, a first stepped-frequency signal is transmitted with the first transmit antenna 610A (610B), a second stepped-frequency signal is transmitted with the second transmit antenna (620B), and a third stepped-frequency signal is transmitted with the third transmit antenna (630B). The transmissions of the three signals (610B-630B) can be conducted concurrently or spaced in time. Also, the three transmit antennas 610A-630A can each be a transmit antenna of separate devices, rather than from a single device 602A (as shown).

In some implementations, the transmissions of the three signals (610B-630B) are all conducted concurrently. In these implementations, the transmit frequencies are made to be different to minimize interference and to facilitate distinguishing between the reflected portions of the signals. For each concurrent transmission, the transmit antennas 610A-630A can each transmit a particular frequency within a predetermined series of frequency steps. Thereafter, each transmit antenna concurrently transmits the next respective frequency of the series. For example, if the frequency series consisted of frequencies $F_1$, $F_2$, and $F_3$, the first transmission may be: $F_1$ for the first transmit antenna 610A, $F_2$ for the second transmit antenna 620A, and $F_3$ for the third transmit antenna 630A. The next transmission can follow as $F_2$ for the first transmit antenna 610A, $F_3$ for the second transmit antenna 620A, and $F_1$ for the third transmit antenna 630A. The physical separation for the three transmit antennas 610A-630A can be used during subsequent processing and/or analysis to account for difference in propagation distance of signals.

If multiple devices are used for transmission, a particular device can be used to so control transmission, detection, and processing. The devices can be networked together (using line or wireless communication) to control flow of information and commands. Specifically, a first device of the multiple devices can direct other devices when and what frequency to transmit, similar to how the device 602A directs the three transmit antennas 610A-630A. The first device can also detect reflected portions of each signal and conduct processing and analysis of the signal transmitted by each of the multiple devices. Also, the first device can receive position information of the other devices to be used during processing and analysis. Results of the processing can be communicated from the first device to each of the other devices, enabling the user of each device to perceive the results.

Reflected portions of the first, second, and third signal are detected using a receiving antenna 605A (640B) and the reflected portions are processed to generate data associated with frequency and phase shifts, using, for example, the techniques described above with respect to elements 420A and 430A of FIG. 4A. As reflected portions of multiple signals of different frequencies may be concurrently received on the same antenna, the signal received by the receiving antenna 605A can be filtered to separately extract the reflected portion of each transmission. For example, in the first transmission in the example above, the signal received by the receiving antenna 605A is filtered with an appropriate filter to extract signals near each of frequencies $F_1$, $F_2$, and $F_3$. In one implementation, the signal received by the receiving antenna 605A is sent to a number of filters equivalent to the number of transmission (in this example, 3 filters), where each filter extracts signal near a particular frequency. In implementations directed to one-at-a-time transmissions, the signal received by the receiving antenna 605A is sent to a single adjustable filter which is adjusted to extract signals near a particular frequency according to the transmitted frequency.

The processed data is analyzed to determine location information of moving objects (660B). If multiple transmit antennas are used (as shown in the diagram 600A), the device 602A takes into account the known distance between the transmit antennas to account for different propagation distances of transmitted signals.

Implementations directed to concurrent transmissions can enable the determination of more precise identification of movement and its location. Using, for example, three transmissions can provide three separate data snapshots of a given scene. These snapshots may each have some differences due to signal noise, unwanted reflection, leakage, or other interference. By averaging the three data sets, the effect of such interference is reduced. Also, targeted or general signal jamming may be present on one, but not all, transmitted frequencies, resulting in very poor data. The device can selectively discard data from one or more transmitted frequencies. Therefore, the use of multi-static motion detection may overcome some effects of jamming.

Also, some implementations directed to one-at-a-time transmission enable a more rapid refreshing of data. In some implementations, the time required to complete the process 400A of FIG. 4A can be too large to update a user of a quickly changing situation. By using multiple transmissions spaced in time according to the length of time required to complete the process 400A, data presented to the user can be updated more often. If, for example, the process 400A requires one half of a second to complete and three separate transmissions are spaced at a half second, data can be refreshed at approximately 6 hertz (depending on processing speed and other parameters, the time required to complete the process 400A may be significantly different than one half of a second).

One-at-a-time refers to the start of transmission and does not preclude the possibility of an overlap between an ending of a first transmission and the start of a second transmission. Also, the order of the elements of process 600B can be different than shown in FIG. 6B. For example, reflected portions of the first signal can be detected using the receiving antenna 605A prior to the transmission of the second stepped-frequency signal with the second transmit antenna 620A.

Finally, the device 602A displays a multidimensional representation indicating the determined location information of the moving object 640A (670B) using, for example, the techniques described above with respect to element 450A of FIG. 4A.

FIG. 7 is a diagram 700 illustrating use of transceivers to conduct interferometric measurement and multi-static motion detection with a scanning device. The device 702 may be implemented as a part of the device 150 of FIG. 1B or other devices. The device 702 includes first, second, and third transceivers 710-730. Each transceiver is configured to both transmit and receive stepped-frequency signals and is spaced from the other transceivers. Therefore, the device 702 is able to conduct multi-static motion detection as described in FIG. 6B of a moving object 740 through transmission by the transceivers 710-730 and to conduct interferometric measurement as described in FIG. 5B of the moving object 740 through signal receipt by the transceivers 710-730. For simplicity, the diagram 700 illustrates the deflected signals but not the three transmitted signals.

In some implementations, the device 702 may use a mix of transceivers with transmit antennas or receive antennas. For example, a device 702 configured to use interferometric measurement as described in FIG. 5B without the need for multi-static motion detection may require three receive antennas but only one transmit antenna. To minimize size, the device 702 can include a transceiver antenna used for all transmission and as a first receive antenna and two spaced receive antennas used as second and third receive antennas in interferometric analysis.

Figure 8A:
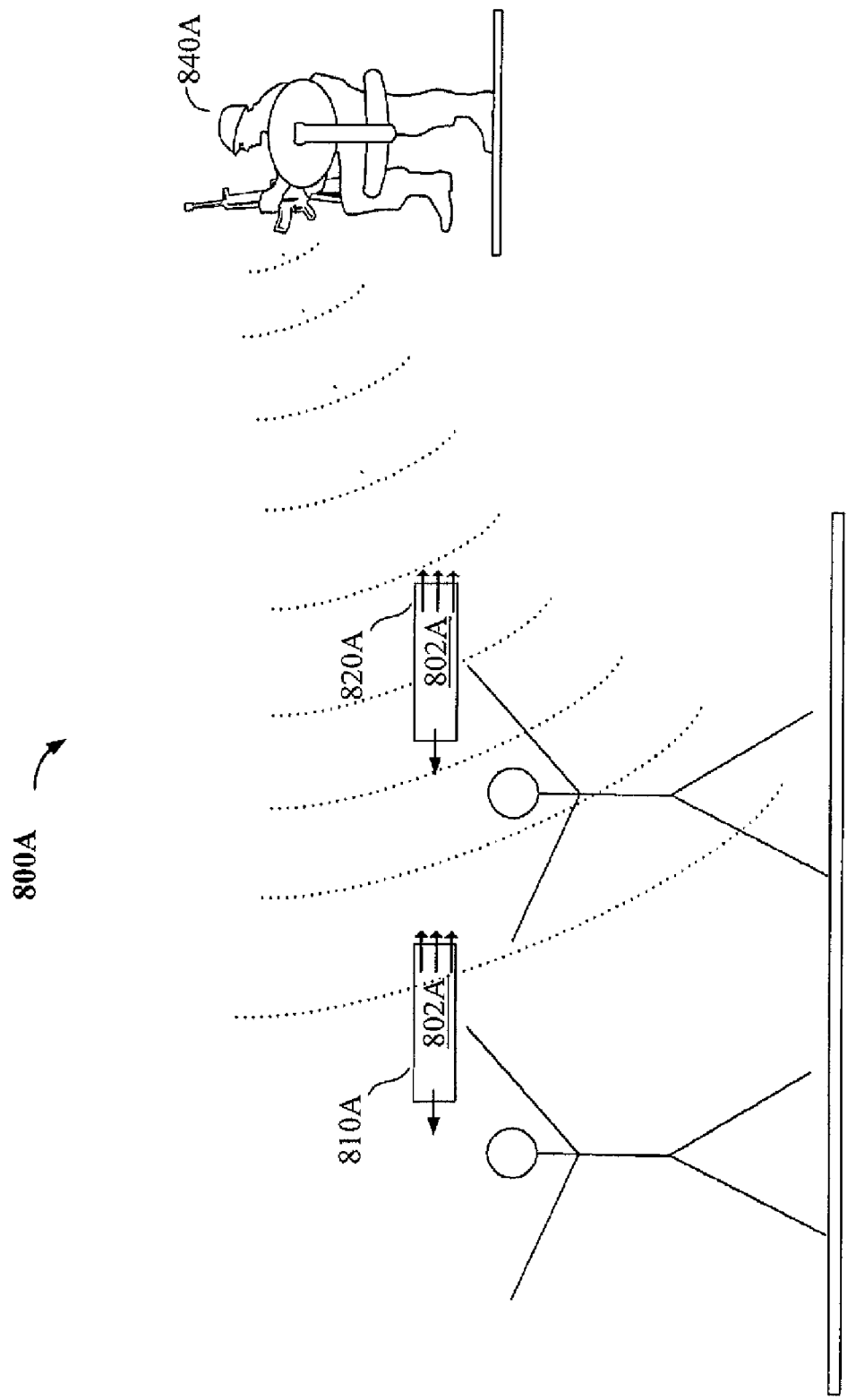
FIG. 8A is a diagram illustrating use of synthetic aperture radar imaging with a scanning device.
Figure 8B:
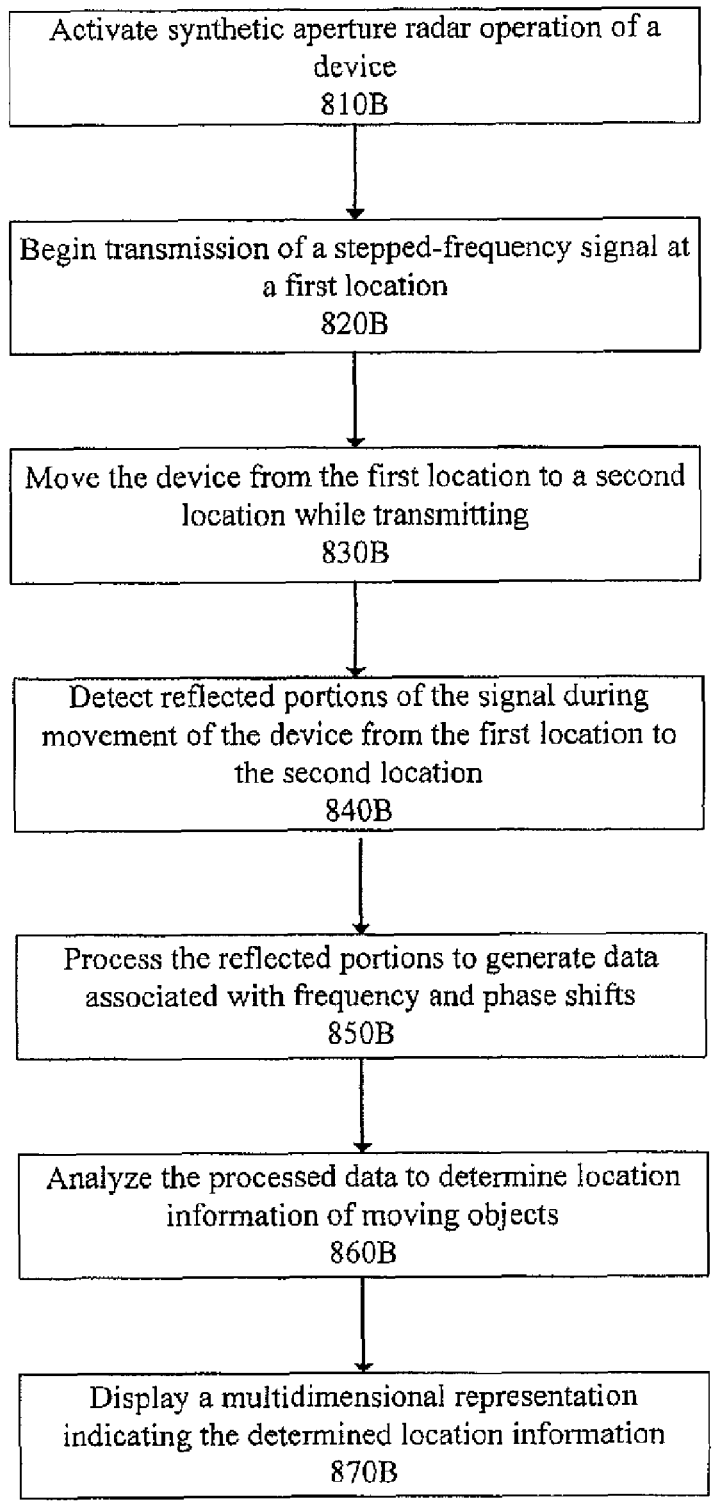
FIG. 8B is a flow chart of an example of a process to detect moving entities using synthetic aperture radar imaging with a scanning device.

FIG. 8A is a diagram 800A illustrating use of SAR imaging with a scanning device 802A and FIG. 8B is a flow chart of an example of a process 800B to detect moving entities using SAR imaging with the device 802A. SAR imaging artificially enhances the effective aperture of the receiving antenna of a device. For example, if SAR data is properly constructed from moving the device a distance of a meter, the results data can correspond to the results obtain from a device with a receiving antenna spanning a meter. The device 802A may be implemented as a part of the device 150 of FIG. 1B or other devices. The process 800B can be used along with or separate from the process 400A of FIG. 4A.

Initially, a SAR operation mode of the device 802A is activated (810B). The activation may be as a result of input by a user to the device 802A to select one of multiple operation modes. For example, in one implementation, the device 802A includes an input option to specify that SAR will be used. In response, the device 802A is triggered to adjust operation according to the description below. In another implementation, SAR operation is the standard mode of the device 802A, and powering on the device 802A activates SAR operation.

Transmission of a stepped-frequency signal begins at a first location 810A (820B). The transmission can begin as a result of user input. For example, the user may activate an input option (the same input option or another input option) to trigger the start of transmission. Also, the transmission may be triggered based upon movement of the device 802A such as that detected from an internal motion sensor. In one implementation, activating the SAR operation mode (810B) initiates device 802A monitoring of movement. When movement is deemed significant (e.g., motion of at least 100 millimeters is detected), transmission of the signal begins (820B). Therefore, when ready, the user can ready the device 802A for SAR operation and begin the scan by beginning the motion of the device (as described below).

The device 802A is moved from the first location 810A to a second location 820A while transmitting the stepped-frequency signal (830B) and reflected portions of the signal are detected during movement of the device from the first location 810A to the second location 820A (840B). The movement can be a lateral movement created by the user to move the device 802A from the first location 810A to the second location 820A. During the movement, the device 802A receives reflected portions of the signal. The reflected portions of the signal may be received and used for subsequent processing along with an indication of where or when the signal was received. Specifically, the device 802A can use time in conjunction with an assumed movement rate or can use measurements from an internal motion sensor to determine the location of the moving antenna at the time reflected portions are detected.

Also, in some implementations, an internal motion sensor is used to provide dynamic SAR scanning. Specifically, the device 802A uses the start and stop of motion to trigger the start and end of transmission/detection. Therefore, a user with ample room to obtain a large aperture can move the device across a longer distance while a user not able to move the device a full meter can nevertheless use space less than a meter to obtain some imaging improvement.

Thereafter, the reflected portions are processed to generate data associated with frequency and phase shifts (850B). The processing can use techniques similar to those discussed in, for example, element 650B of FIG. 6B. The reflected portions may be received and processed into discrete packets of data associated with frequency and phase shifts. The packets can be associated with a relative position in the movement. Implementations with an internal motion sensor can use motion information to trigger generation of packets at specific physical intervals and record the location of each packet based on sensed motion. For example, in one implementation, a packet is recorded every half wavelength (e.g., at approximately every 2.5 inches) across one foot of lateral device motion based upon internal motion sensing. Implementations not employing motion sensors can be configured to assume movement of a particular speed for the purposes of packet location determination, and the user can be trained to move the device 802A at approximately the assumed speed.

The processed data is analyzed to determine location information of moving objects (860B) and a multidimensional representation indicating the determined location information is displayed (870B), using, for example, the techniques described above with respect to elements 440A and 450A of FIG. 4A.

Figure 9A:
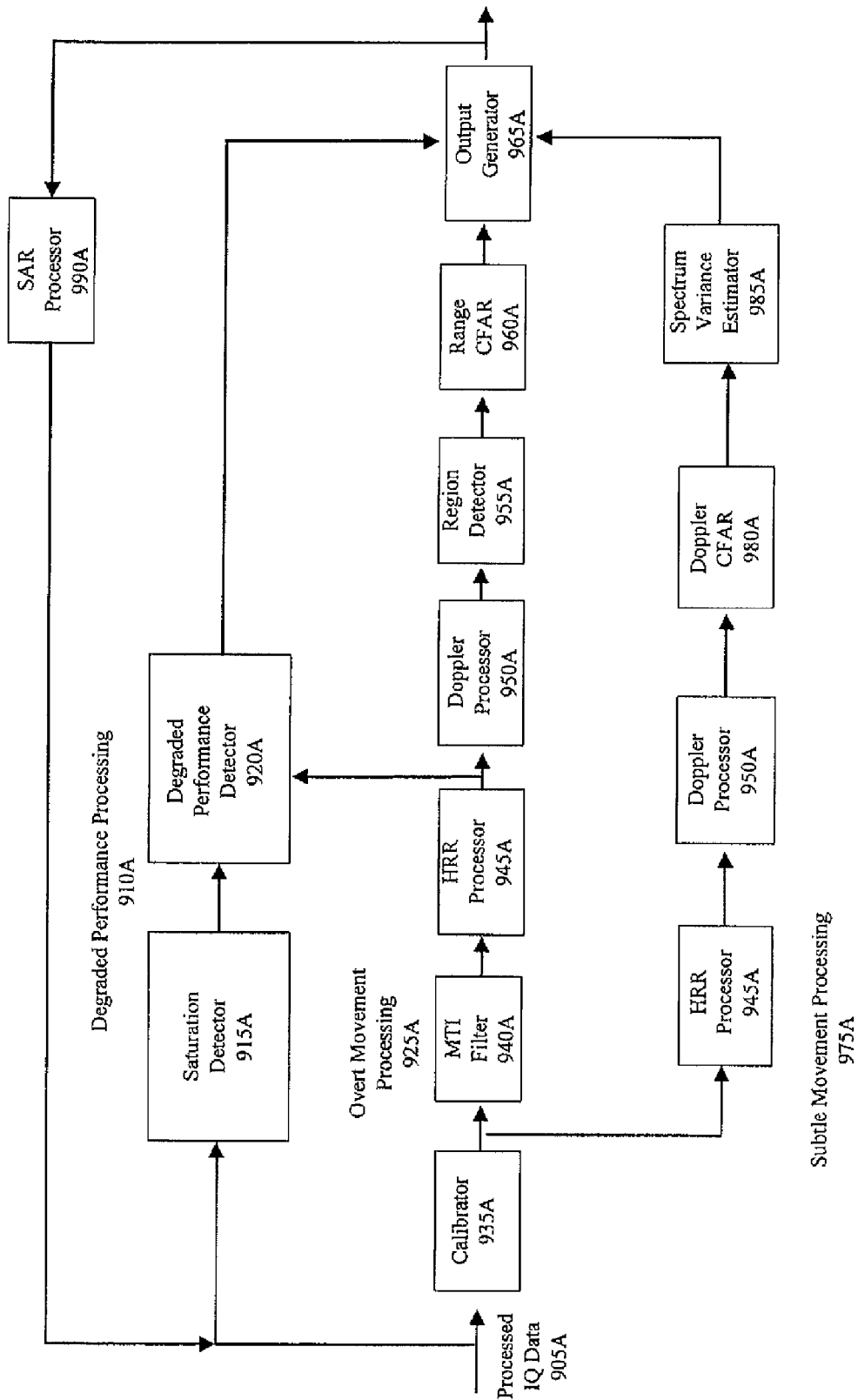
FIG. 9A is a flow chart of an example of a process to analyze data associated with frequency and phase shifts generated by a scanning device.

FIG. 9A is a flow chart of an example of a process 900A to analyze data associated with frequency and phase shifts generated by a scanning device. In various implementations, the process 900A is carried out with the device 150 of FIG. 1B and can be used to perform element 440A of FIG. 4A, element 440B of FIG. 4B, element 560B of FIG. 5B, element 660B of FIG. 6B, or element 860B of FIG. 8B. For brevity, however, the process 900A is described with respect to element 440A of FIG. 4A.

The process 900A receives processed IQ data that may be generated, for example, by element 430A of FIG. 4A and with the circuit 300 of FIG. 3. As shown, the process 900A involves multiple signal processing paths, degraded performance processing (910A), overt movement processing (925A), and subtle movement processing (975A). For simplicity, the signal processing paths are discussed separately, though the different types of processing may be concurrently carried out on the same input signals. Also, paths shown are examples only. Other implementations may conduct processing along a single path configured to process overt or subtle movement. Each processing path may be associated with a specific type of result displayed from the output generator (965A). In various implementations, in both overt movement processing (925A) and subtle movement processing (975A), phase and/or frequency data for each transmitted frequency is first used to develop a current picture of an environment, and is then compared against further phase and frequency data to determine differences.

The process 900A incorporates coherent integration gain and robust detection algorithms, to provide enhanced range of movement detection, higher probability of detection (Pd), and a lower probability of false alarm (Pfa). The process 900A begins when IQ data is input to be processed (905A). The input IQ data can be the output of the mixer 350 of the circuit 300 of FIG. 3. In some implementations, the IQ data is generated using a single transmit antenna and a single receive antenna. In other implementations, the IQ data is generated using multiple transmit antennas for interferometric processing and/or multiple receive antennas for multi-static processing. Accordingly, the process 900A can be used to implement portions of the processes 500B of FIGS. 5B and 600B of FIG. 6B.

In various implementations, the user inputs one or more commands associated with one or more of overt movement processing (925A), subtle movement processing (975A), or both. For example, a user wishing to target only subtly moving objects (e.g., the cardio-pulmonary function of an individual sleeping or in a coma), may activate an input option to trigger the device to conduct subtle movement processing (975A) where it otherwise would not occur. In various implementations, a single command may be pressed, which may, depending on the reflected signal, trigger overt moving processing (925A), subtle movement processing (975A), or both.

IQ data is input to a calibrator (935A) and to a saturation detector (915A). The saturation detector (915A) sends data to a degraded performance detector (920A), which monitors for situations including detection of A/D converter saturations or unusually high signal levels that may arise from the transmitted signal reflecting off metal objects buried within or behind walls, detection of significant increases in the noise floor resulting from intentional or unintentional jamming, and detection of significant signal energy across all range cells associated with excessive movement of the antenna. If such situations are detected, the degraded performance detector (920A) can determine that the transmission waveform of subsequent transmission should be altered according to element 410B of FIG. 4B. Also, data from the degraded performance detector (920B) can be sent to the output generator (965A) to trigger a visual indication or an alert to specify the detection of a degraded signal. The alert may signify to the user that processing results may be less reliable. Degraded performance processing (910A) need not interrupt other processing.

In overt movement processing (925A), the IQ data may first be sent through the calibrator (935A). Calibration can be used to minimize the effects of non-ideal transceiver hardware, such as transmit-to-receive signal leakage, unwanted device movement, interference, or other adverse effects upon the IQ data or collection thereof. Target detection performance may be improved as a result of cleaner range and Doppler profiles. Calibration can provide for adjustment of the collection of data, by, for example triggering the determination that the transmission waveform of subsequent transmission should be altered according to element 410B of FIG. 4B. Calibration can also provide for adjustment of collected data, to for example, compensate for direct-current (DC) offset errors, IQ gain and phase imbalance, and gain and phase fluctuation across frequency which may be caused, for example, by transmit-to-receive signal leakage or unwanted device movement. In various implementations, calibration can be conducted at other positions within the process 900A. Hardware support for calibration can include use of an internal motion sensor and signal processor, solid state RF switches in the receive and transmit antenna front end(s) that enable the receiver input to be switched from the antenna to either resistive load or to a reduced power sample of the transmit signal. Calibrated data may be used in overt movement processing (925A) and subtle movement processing (975A).

The overt movement processing (925A) can be optimized for rapid detection of moving personnel. Processing delays associated with filtering and coherent integration can be short, enabling quicker display/alert of indications of detected movement, for example, within less than a second of the event in some implementations. The overt movement processing (925A) can begin with the data output from the calibrator (935A) input to the moving target indication (MTI) filter (940A) to eliminate or flag strong returns from stationary clutter, or returns from objects within a proximity from the device (e.g., objects on the same side of a wall as the device). Flagged returns from the MTI filer (940A) can be used by the output generator (965A) to identify flagged objects accordingly. For example, in one implementation, objects flagged as stationary are presented with a characteristic (e.g., a color or uniquely shaped icon) which differs from objects not flagged as stationary and object flagged as likely repeated mechanical movement are similarly presented with a different characteristic. Each transmit frequency may be processed by a separate filter having a bandpass response that passes signals from separate target velocities. Separate filters may enable detection of short duration movements from the arms and legs of stationary personnel as well as the detection of the main body movement, such as walking and running.

The data output from the MTI filter (940A) is input to the high range resolution (HRR) processor (945A). In one implementation, the HRR process (645A) uses an inverse fast fourier transform (IFFT) to transform the ensemble of returns from the received signal to HRR profiles. In other implementations, other transforms may be used. Depending on the characteristics of the results, the HRR process (945A) results may be input to the degraded performance detector (920) as well as the Doppler processor (950A). The Doppler processor (950A) may provide additional coherent integration gain to further improve the signal-to-noise ratio. A region detector (955A) then selects a Doppler bin with amplitude regions from range resolution cells.

The region amplitudes are passed on to a Range constant false alarm rate processor (CFAR) (960A). The Range CFAR (960A) is a cell-averaging constant false alarm rate (CA-CFAR) detector and operates along the HRR range cells output from the region detector (955A). The range cells are compared to the surrounding cells. A detection may be sent to the output generator (965A) if calculated parameters of the cell under test are greater than a predetermined amount.

Subtle movement processing (975A) is optimized for detection of stationary personnel, such as individuals whose only significant movement is that caused by respiratory and/or cardiac function. Subtle movement processing (915A) includes the calibrator (935A), the HRR processor (945A) and the Doppler processor (950A), but with longer integration times. A longer integration time provides fractional-hertz Doppler resolution to resolve the carrier modulation sidebands associated with breathing. The HRR processor (945A) can be used directly on the calibrated radar data, bypassing the MTI filters that may otherwise remove the respiration sidebands.

In subtle movement processing (975A), the output of the Doppler processor (950A) is sent to a Doppler CFAR processor (980A). The Doppler CFAR processor (980A) may be applied across the Doppler processor (950A) output to identify portions of the spectrum that are significantly above the noise floor. Values selected by the Doppler CFAR processor (980A) may be input to the spectrum variance estimator (985A) where the power-weighted second-moment of the spectrum is determined. If the calculated spectrum variance is within limits typical of respiration, the output generator (965A) may declare detection of subtle movement.

The output generator (965A) receives the results of the analysis of the IQ data from one or more of the overt movement processing (925A), subtle movement processing (975A), and the degraded performance processing (910A). For example, IQ data may be analyzed according to each processing path, generating multiple sets of results. The output generator (965A) may give priority, such that, if the same object is identified as overt and subtle movement, the output generator (965A) considers the object overtly moving. The output generator (965A) may perform additional clean-up of the detection map, including, for example, removal of detections beyond a range, and encoding the detection as either near or far. In some implementations, the output generator (965A) constructs a graphic user interface (GUI) to render the results for display to the user. The GUI can show a two or three dimensional representation of the detected objects as described with respect to the display screen 119 of FIG. 1 and/or element 450A of FIG. 4A.

The output generator (965A) can output results of signal processing to a SAR processor (990A). The SAR processor (990A) is used as a feedback loop in implementing portions of the process 800B of FIG. 8B. Specifically, the SAR processor (990A) receives the output of the output generator (965A) and outputs SAR processing data as further IQ data for subsequent processing using the process 900A to provide a radar image with a synthetic aperture.

The above process 900A is an example and other processing techniques could be used along with or separate from elements of the process 900A. For example, alternate techniques discussed in FIG. 4A, such as Maximum Likelihood Method, Maximum Entropy Method, or Music Method, may offer greater resolution for micro-Doppler detection using shorter observation times. Also, methods such as Singular Spectrum Analysis (SSA) and Higher-order statistics based techniques (e.g., Bispectral Analysis) can also be used to better resolve very closely spaced independent target returns than is possible with direct Fourier methods. Further, other methods that focus on reducing the computational cost relative to the FFT methods can be used to create the frequency (Doppler) spectrum, such as, Discrete Cosine Transform, Fast Hartley Transform, and Walsh-Hadamard Transform.

Figure 9B:
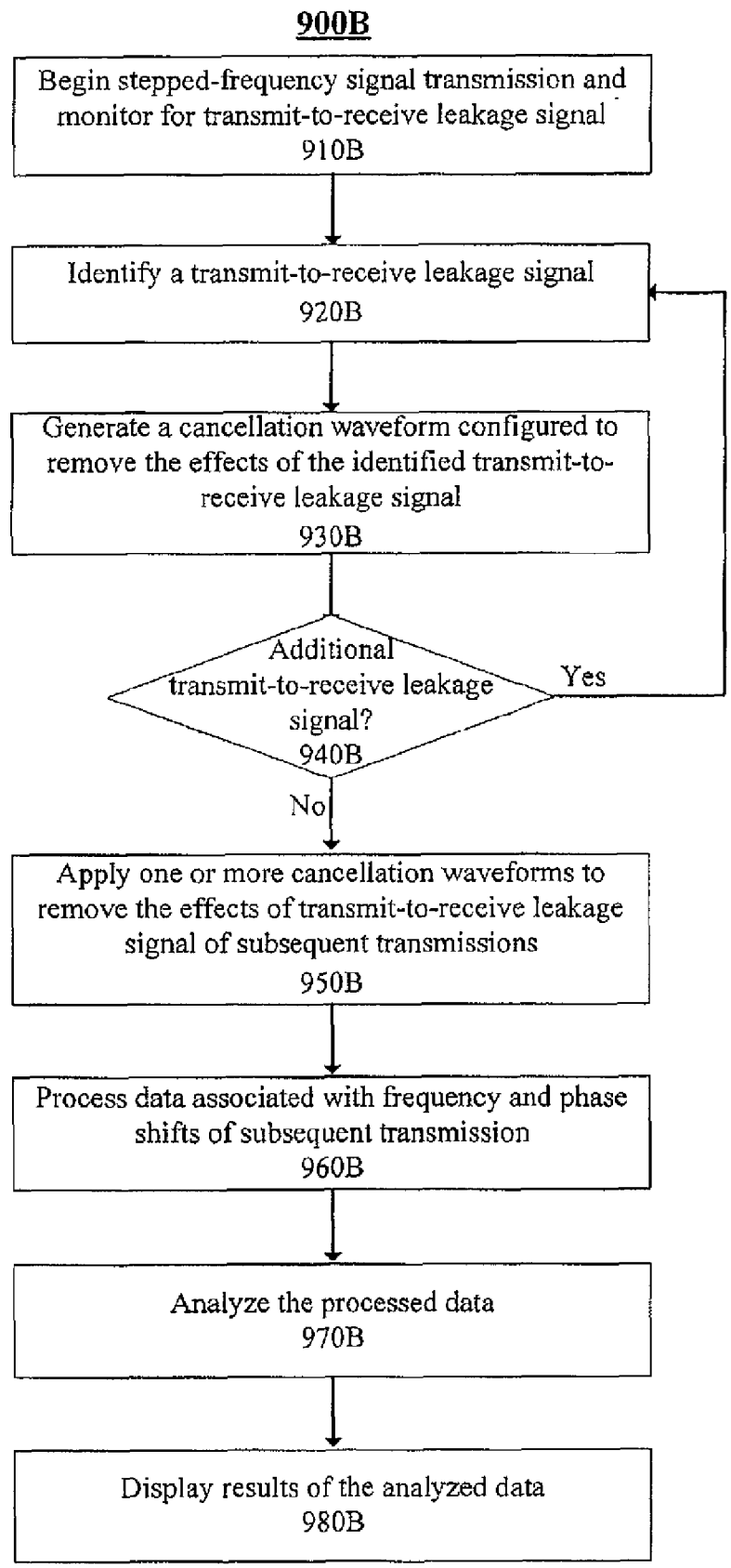
FIG. 9B is a flow chart of an example of a process to cancel transmit-to-receive leakage signal with a scanning device.

FIG. 9B is a flow chart of an example of a process 900B to cancel transmit-to-receive leakage signal with a scanning device. This processing approach can be used to adaptively locate and remove various components of the transmit-to-receive leakage signal, which generally are orders of magnitude higher in amplitude then the highest reflected portions of signal intended to be detected. This cancellation can reduce the dynamic range of the signal data and also can suppress the range sidelobes of the leakage signal which otherwise may obscure lower-amplitude stationary targets. A reduction of dynamic range can allow for increased magnification of data for better separation between noise and targets without generating significant artifacts that would otherwise be generated by the increased magnification. The process 900B may be implemented as a part of the process 900A of FIG. 9A and/or the process 400A of FIG. 4A. For example, the process 900B can be used as part of the calibrator (935A) in FIG. 9A. Also, the process 900B may be performed using the device 150 of FIG. 1B or other devices.

The device begins stepped-frequency signal transmission and monitors for transmit-to-receive leakage signal (910B). The monitoring may begin concurrently with the transmission or just before or after the transmission. In one implementation, the monitoring begins prior to transmission. Thereafter, the change in received signals is used to determine the presence of transmit-to-receive leakage signal according to the techniques described below.

From the monitoring, a transmit-to-receive leakage signal is identified (920B). The identification can be based upon various characteristics in signal received by one or more receive antennas that are indicative of transmit-to-receive leakage. For example, due to the proximity of the receive antennas to the transmit antennas, transmit-to-receive leakage signal can be the strongest received signal within a short delay from transmission. Specifically, transmit-to-receive leakage can occur at effectively zero distance from the device. Therefore, signal reflected from locations within a short distance (e.g., less than one foot) can be identified as transmit-to-receive leakage (920B).

Amplitude can also be used to identify transmit-to-receive leakage signal. In particular, transmit-to-receive leakage signal can dominate the dynamic range with an atypically high amplitude (e.g., several orders of magnitude greater than the highest amplitude reflected signal). This effect is a result of the differing paths of signals. Specifically, because the transmit-to-receive leakage signal often is from a direct path and signals reflected from moving objects often move through an attenuating medium (e.g., a wall) there can be a significant difference in amplitude between transmit-to-receive leakage signal and signal reflected from moving objects.

Another characteristic that can be used to identify transmit-to-receive leakage signal is phase change. Generally, transmit-to-receive leakage signal exhibits no Doppler shift. The lack of a Doppler shift is because transmit-to-receive leakage signal is reflected from the device and received at the device. Therefore, the transmission location and receive location have no difference in net movement so long as they are mechanically connected.

A cancellation waveform configured to remove the effects of the identified transmit-to-receive leakage signal is generated (930B). The cancellation waveform is configured to offset the effect, thereby effectively removing the identified transmit-to-receive leakage signal. In particular, a signal profile which is the inverse of the profile of the identified transmit-to-receive leakage signal can be created. This cancellation waveform can effectively zero out the transmit-to-receive leakage signal.

These techniques can be applied iteratively to maximize the reduction of interference caused by transmit-to-receive leakage. For example, after generating the cancellation waveform, the device determines whether there is additional transmit-to-receive leakage signal (940B). If there is additional transmit-to-receive leakage, the process 900B identifies and generates a cancellation waveform to remove effects of the additional transmit-to-receive leakage signal (920B and 930B). The iteration can be used to fine-tune the removal of a particular signal leakage path or to remove signal from multiple leakage paths. For example, signal from a separate leakage path may travel further before reaching the receive antenna and may not have the same amplitude or delay. Multiple cancellation waveforms can be generated, or a single cancellation waveform can be adjusted with each iteration.

The one or more cancellation waveforms are applied to remove the effects of transmit-to-receive leakage signal of subsequent transmissions (950B). For example, the cancellation waveform can reflect the signal profile of the identified transmit-to-receive leakage signal and may be stored in memory and used during calibration processing of later data to effectively remove subsequently occurring transmit-to-receive leakage signal. In various implementations, the one or more cancellation waveforms are applied to all subsequent transmission while the device is powered on. In other implementations, the process 900B is repeated at fixed intervals of time or upon detection of poor data, such as, for example, by the saturation detector (915A) or the degraded performance detector (920A) of FIG. 9A. Thereafter, data associated with frequency and phase shifts of the subsequent transmission is processed, the processed data is analyzed, and results of analyzed data are displayed (960B-980B) using, for example, the techniques described above with respect to elements 430A-450A of FIG. 4A.

Figure 9C:
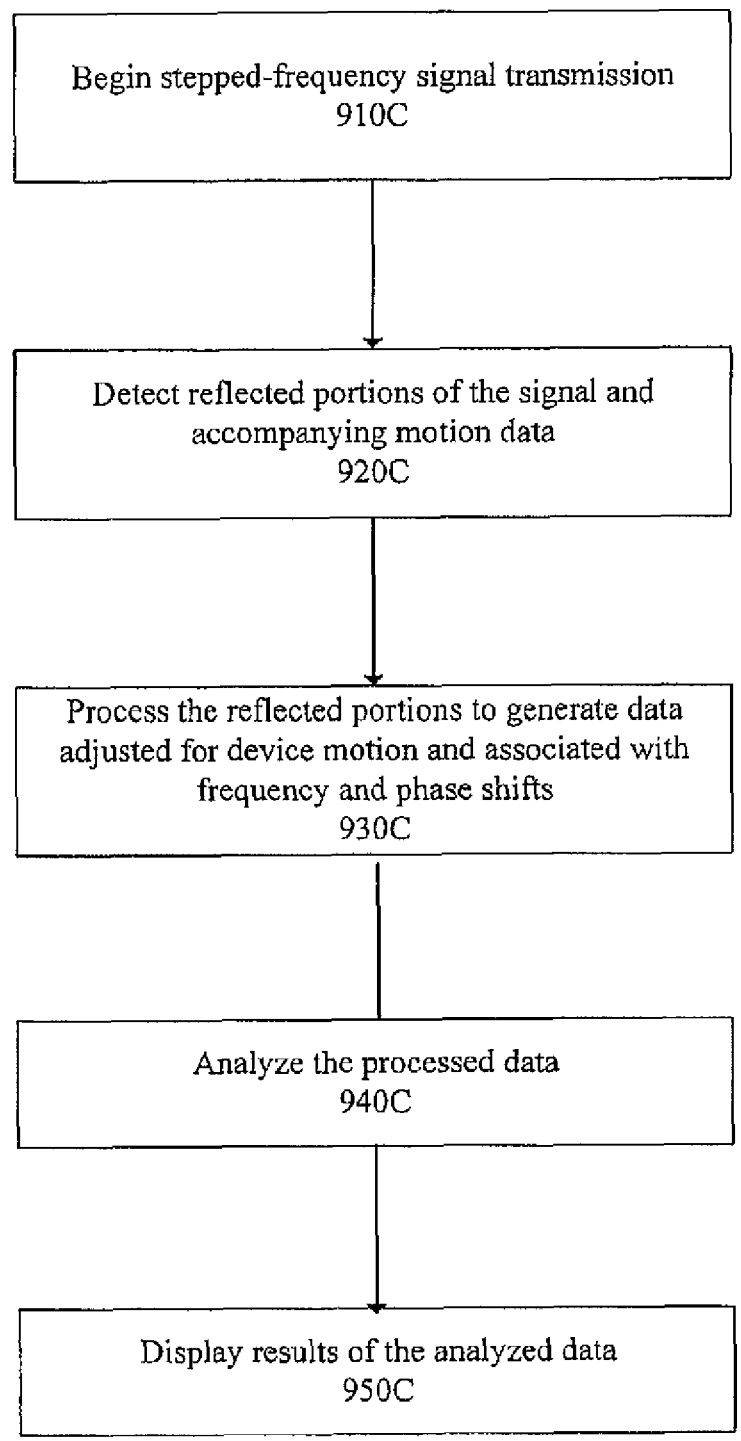
FIG. 9C is a flow chart of an example of a process to compensate for motion occurring during operation of a scanning device.

FIG. 9C is a flow chart of an example of a process 900C to compensate for motion occurring during operation of a scanning device. This processing approach can be used to enable the operation of the device while it is being moved intentionally or unintentionally. Specifically, input from a motion sensor is used to facilitate the adjustment of data to offset the effect of device movement. The process 900C may be implemented as a part of the process 900A of FIG. 9A and/or the process 400A of FIG. 4A. For example, the process 900C can be used as part of the calibrator (935A) in FIG. 9A. Also, the process 900C may be performed using the device 150 of FIG. 1B or other devices.

The device begins stepped-frequency signal transmission (910C) and reflected portions of the signal and accompanying motion data are detected (920C). Device movement can contribute to or otherwise alter the phase change of the reflected portions created by the movement of the reflecting object. Specifically, if the device is moving towards a stationary object (e.g., due to unintentional device movement), the reflected portion of the signal can exhibit a Doppler shift similar to what would be exhibited if, instead, the object had been moving towards the stationary device. The movement information enables adjustment for phase changes resulting from this device movement. In various implementations, as reflected portions of the signal are received and sent for processing, the device receives movement information from an internal inertial sensor. In other implementations, the device uses a GPS sensor to derive device movement alone or in conjunction with an internal inertial sensor.

The reflected portions are processed with the movement information from the internal motion sensor to generate data adjusted for device motion and associated with frequency and phase shifts (930C). In one example, processing includes generating a packet of data for received reflections of each frequency step of a sequence of frequency steps in the transmitted stepped-frequency signal and associating motion information with each packet. In particular, if an internal inertia sensor is used, the output of the sensor can be sampled once for each packet to determine acceleration of each of three axes. This acceleration information can be accumulative and can be integrated across multiple packets for determination of velocity and direction of movement. From the determination of velocity and direction of movement, the generated data can be adjusted to reverse the Doppler effect resulting from the motion of the device with respect to the detected reflections. Also, if a GPS sensor is used, the position as determined by the sensor can be sampled once for each packet. This position information can be used to determine velocity and direction of movement by comparing previous position information.

The processed data is analyzed (940C). The motion determined by the motion sensor can be used during analysis to compensate or offset the perceived Doppler shift (and thus the perceived motion) of an object detected by the device. Thereafter, results of analyzed data are displayed (950C) using, for example, the techniques described above with respect to element 450A of FIG. 4A.

Alternatively or in conjunction, adaptive processing of the radar return can be used by the motion sensor 190 and/or the signal processor 175 to estimate the sensor motion. The latter approach can be employed to utilize the phase change of stationary scattering present in the scene to estimate the sensor motion.

Figure 9D:
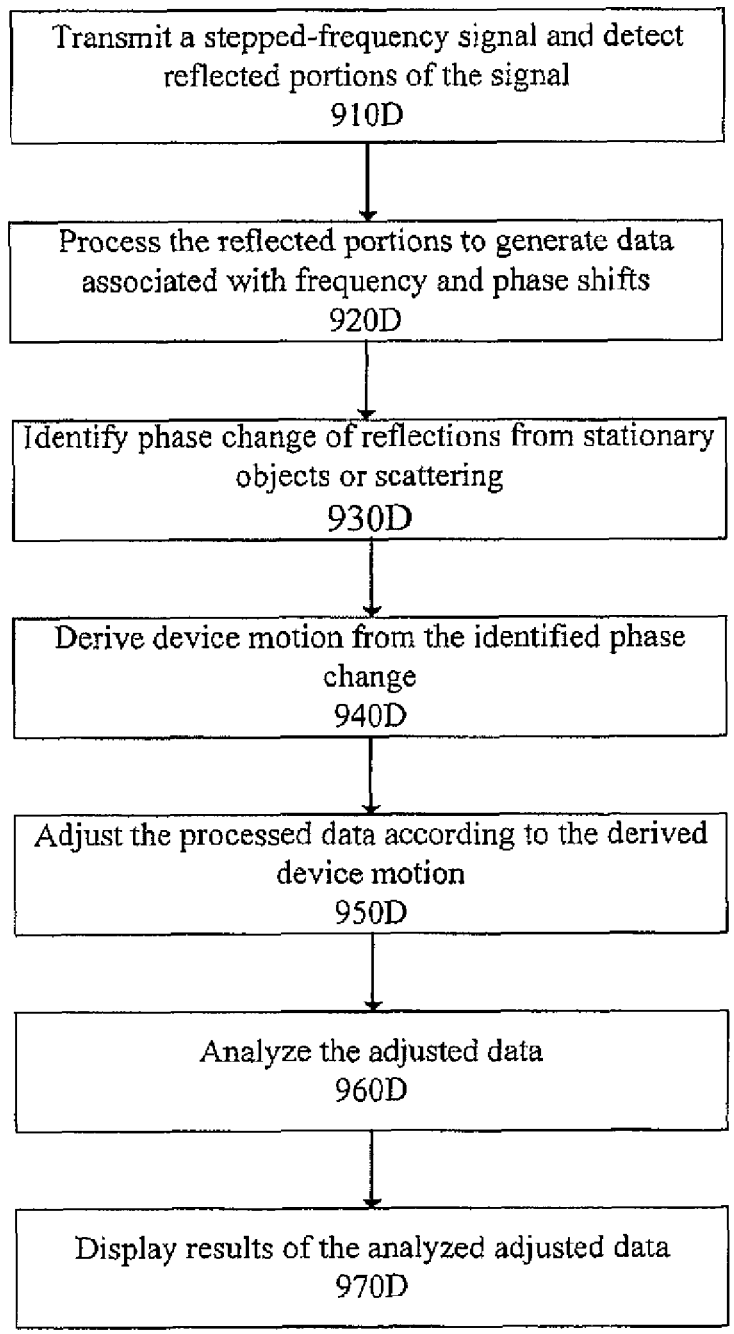
FIG. 9D is a flow chart of an example of a process to compensate for motion occurring during operation of a scanning device using adaptive processing.

FIG. 9D is a flow chart of an example of a process 900D to compensate for motion occurring during operation of a scanning device using adaptive processing. This processing approach can be used to enable the operation of the device while it is being moved intentionally or unintentionally without the use of a motion sensor. Specifically, the device analyzes data for the appearance of movement of stationary objects and uses the apparent movement to derive and compensate for the actual movement of the device. The process 900D may be implemented as a part of the process 900A of FIG. 9A and/or the process 400A of FIG. 4A. For example, the process 900D can be used as part of the calibrator (935A) in FIG. 9A. Also, the process 900D may be performed using the device 150 of FIG. 1B or other devices. Finally, the process 900D can be used in conjunction with an internal motion sensor as described in the process 900C of FIG. 9C to further minimize the effects of device motion.

The device transmits a stepped-frequency signal and detects reflected portions of the signal (910D). The reflected portions are processed to generate data associated with frequency and phase shifts (920D). As discussed above, the phase of reflected portions of the signal may exhibit a Doppler shift based on the relative movement of the object towards or away from the device. If the device is moving towards a stationary object, the reflected portion of the signal can exhibit a Doppler shift similar to what would be exhibited if, instead, the object had been moving towards the stationary device.

The device identifies a phase change of reflections from stationary objects or scattering (930D). In one implementation, the identification of the phase change can be based upon perceiving newly occurring movement (or a phase change indicative thereof) from a reflection from a previously stationary object. For example, the device can identify non-moving objects or objects of repeated mechanical movement and store the identification in memory. Thereafter, the device can compare the stored identification of the prior identified stationary object with the object's apparent movement during a subsequent transmission. From this comparison, the device can identify a phase change of reflections from stationary objects or scattering (930D).

Also, in various implementations, the device can identify the phase change by analyzing a commonality in the data of reflected portions of the signal last transmitted. Specifically, the device can look for consistent movement or a pattern of movement of scattering or objects which reflect the transmission. For example, if the majority of reflected portions of the signal indicate movement (i.e., exhibit a phase change), the device can determine that the phase change of the reflected portions of the signal is a phase change of stationary objects. Finally, some implementations use a combination of the two approaches described above. For example, the device can first determine if there is common movement for a current set of objects, and, if so, compare the prior and current movement of specific objects to identify the phase change of reflections from stationary objects (930D).

Next, the device derives device motion from the identified phase change (940D). Specifically, the device determines what motion of the device would produce the identified phase change of the stationary objects. For example, in some implementations which generate a packet of data for received reflections of each frequency step, an adjustment is associated with each packet indicating the derived motion. The derived motion can be both a velocity and direction. To derive both velocity and direction, the device may process the perceived motion towards and away from multiple objects of different physical locations. This may include interferometric processing techniques to determine movement of the device in three spatial dimensions.

Thereafter, the processed data is adjusted according to the derived device motion (950D). The adjustment can include altering frequency data to counteract the effect of the motion derived to have occurred for the device. Finally, the adjusted data is analyzed (960D) and results of the analyzed adjusted data are displayed (970D) using, for example, the techniques described above with respect to element 450A of FIG. 4A. The adjustment may be conducted later in processing only for specific objects of significance or may be conducted earlier in processing on the data used to determine the existence of moving objects.

FIGS. 10A-12B and the discussion below are directed to a set of specific implementations of a scanning device referred to as a wall penetrating personnel detection sensors (WPPDS) and are provided as one possible set of implementations of a sensor for detecting moving entities as described above.

In one implementation, a WPPDS employs a through-wall-detection radar device to detect personnel. The device includes a light-weight (e.g., a few pounds or less), portable, dedicated through wall device for detection through walls. Particular implementations of the WPPDS are configured to detect both moving and stationary (breathing) personnel and can be useful in a variety of situations. For example, an individual buried under structural debris can be located with relative spatial position or distance and angle, which may be critical to a life saving operation. Also, in the case of hostage situations, the WPPDS may be used to determine the position of individuals from certain locations, which may dictate the rescue operation methodology.

A particular implementation employs an AN/PSS-14 mine detection radar device in a miniaturized WPPDS unit that fits into a semi-automatic weapon (SAW) ammo pouch, and may operate for 180 twenty-second cycles and otherwise remain on standby during a 16 hour period running on eight disposable AA batteries. Other implementations use different batteries. For example, one implementations uses six CR123 type camera batteries rather than eight AA batteries. The WPPDS detects moving targets particularly well through non-metallic materials (e.g., cement blocks, reinforced concrete, adobe, wallboard and plywood).

The WPPDS may employ coherent, stepped-frequency continuous wave (SFCW) radar that provides excellent through wall detection performance. Detection is realized through range-Doppler processing and filtering to isolate human motion.

In various implementations, data from a SFCW radar may be processed as an ensemble of fixed-frequency CW radars, allowing for the optimum detection of the Doppler shift of a moving target over time via spectral analysis. The stepped-frequency radar data may also be processed to compress the bandwidth and obtain a high range resolution profile of the target. For example, the data may be processed to remove stationary or fixed time delay data, leaving the moving target data to be evaluated in both the range and Doppler (velocity) dimensions. A coherent frequency-stepped radar may have an advantageous signal gain when computing the range and Doppler values of moving targets. Pulse type or frequency chirp type radars may not be able to achieve the same integrated signal gain as stepped-frequency radar, due to a non-coherent nature.

Another property of a SFCW radar is the ability to operate in environments that exhibit high radio frequency interference (RFI). Short pulse and frequency chirp radar devices maintain a wider instantaneous receive bandwidth, enabling more RFI into a processing electronics chain and reducing the signal to noise/interference level, which may reduce sensitivity and may degrade detection performance.

In one implementation, the SFCW radar device enables detection of subtle and overt movement through walls. The SFCW radar device can use processes that operate on hardware that is generally commercially available. The architecture of the SFCW radar device generally is less susceptible to jamming (intentional or unintentional) than other radar architectures. Additionally, the reduced bandwidth enables implementation of more highly integrated RF technology, resulting in a reduction in device size, weight and DC power.

With respect to the antenna, the antenna elements can be miniaturized (scaled) versions of the AN/PSS-14 cavity-backed spiral design. The miniaturized tactical antenna supports the selected frequency range (the upper end of the AN/PSS-14 operating range, which improves performance against rebar) and packaging constraints.

The RF Electronics can generate the frequency-stepped radar waveform, amplify the signal for transmission, receive energy reflected off targets using a low-noise front end, and generate coherent (in-phase and quadrature, or I & Q) signals used in the detection process. The transceiver electronics feature a reduced bandwidth, which enables a single voltage controlled oscillator (VCO) implementation compared to a more complex two VCO design. Further device miniaturization can be achieved through implementation of a direct down-conversion (homodyne) receiver.

A brassboard homodyne receiver has shown that significantly increased detection range in through wall applications is achievable compared to the phase-noise limited AN/PSS-14 super-heterodyne architecture. The reduced bandwidth of the single-board TX/RX can provide sufficient range resolution capability to support detection and can avoid the National Telecommunications and Information Administration (NTIA)/Federal Communication Commission (FCC) restrictions associated with ultra wideband (UWB) radars. The transmit power, coupled with the gain of the antenna, can result in a low radiated power (approximately the same as cell phones), making the device safe for human exposure. Some implementations use a super-heterodyne receiver with common transmit and receive local oscillators and VCOs. The super-heterodyne implementations can reduce phase noise as compared to the homodyne implementations.

The digital signal processor (DSP) hosts the motion detection algorithms. The WPPDS signal processing algorithm incorporates coherent integration gain and robust detection algorithms, achieving superior performance with greater detection range, higher probability of detection (Pd), and lower probability of false alarm (Pfa). Particular implementations may be used to scan through damp concrete blocks and rebar, so as to permit ready detection of moving personnel.

The device also can include power supply circuitry needed to convert 6V battery power for the electronics. Bottoms-up power consumption calculations show that a set of disposable AA alkaline batteries may provide 180 twenty-second operating cycles. The low power, compact, high-performance direct-conversion radar transceiver can be realized through use of RF Monolithic Microwave Integrated Circuits (MMICs) and the RF integrated circuits available. An ultra-low phase noise Temperature Compensated Crystal Oscillator (TCXO) housed in a miniature surface-mountable package can be used as a reference to a synthesizer chip with a VCO integrated on the chip. Loop response time and phase noise can be achieved and optimized via an external loop filter, creating a stable, fast-locking signal source with low divider noise.

The signal source is then amplified by high-efficiency monolithic amplifiers with integrated active biasing circuitry and on-wafer DC blocking capacitors. This approach minimizes part count and current consumption. This low-noise VCO is also used in the demodulation of the received radar return, which provides considerable phase noise cancellation due the oscillator coherency. With much lower phase noise riding on returned signals (including near-wall reflections), the receiver sensitivity can be predominantly limited by thermal noise, enabling increased detection range compared to the AN/PSS-14 radar receiver. This also enables an increase in transmit power for increased range.

The direct-conversion quadrature demodulator can include polyphase filters and ensure quadrature accuracy across the entire bandwidth. Pre-amplification of the LO and integrated variable gain control of the demodulated signal can allow for efficient use of circuit board real estate and provide the device with signal conditioning flexibility to maximize signal dynamic range at the analog-to-digital (ADC) inputs.

The digital signal processor (DSP) is used to process IQ data from the radar transceiver to determine if objects are in motion and, if so, to alert the user. The DSP can have many features for power management, including dynamic frequency control, dynamic core voltage control, and the capability of turning off unused sections of the IC. These power management features make this DSP an excellent choice for battery operated WPPDSs. Operating the WPPDS at half the frequency and a core voltage of 1V allows lowering of the power and can enable a programmable performance upgrade for the future. A clock frequency is provided by the RF transceiver board via a Low-voltage differential signaling (LVDS) differential clock driver. This helps protect signal integrity and reduces electromagnetic interference (EMI) caused by the fast clock edge rates.

In various implementations of WPPDS, the design features 8 M bytes of synchronous dynamic random access memory (SDRAM) for fast program access and enough storage for 60 seconds of captured data per operating cycle. In addition, 4 M bytes of flash memory are used for booting up the DSP and for non-volatile storage. A universal serial bus (USB) interface is used as a test port, and will only be powered up for debugging and data collection. An ADC includes an 18 bit ADC that allows a 15 dB increase in signal-to-noise ratio (SNR) to take advantage of the increased dynamic range and sensitivity. Differential inputs improve common-mode noise cancellation, allowing for a more sensitive detector. The op-amps are selected for low power, low noise performance as amplifiers and active filters. A 16 bit DAC is used to cancel the DC offset from the incoming IQ signals from the RF Electronics. Serial communication protocol (SPI) is used to communicate with the ADC, digital-to-analog converter (DAC), and RF phase-locked loop (PLL), which helps reduce I/O requirements and EMI.

Figure 10A:
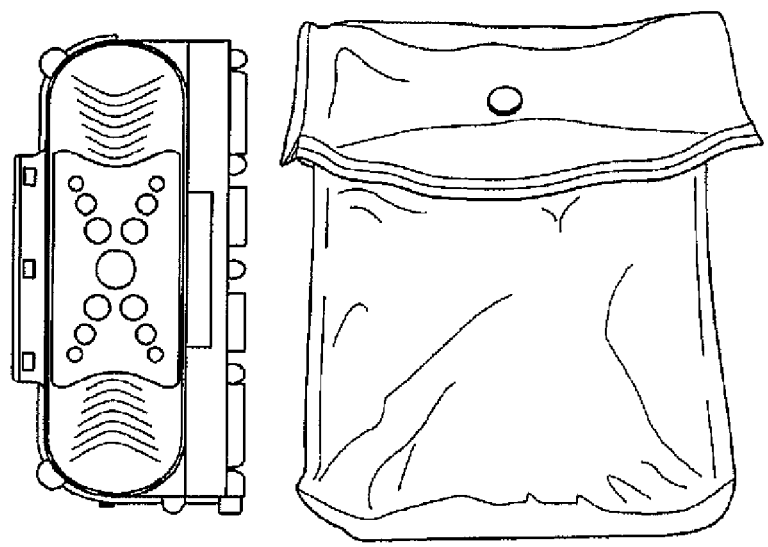
FIG. 10A is a picture of a handheld stepped-frequency scanning device relative to a semi-automatic weapon ammo pouch.
Figure 10B:
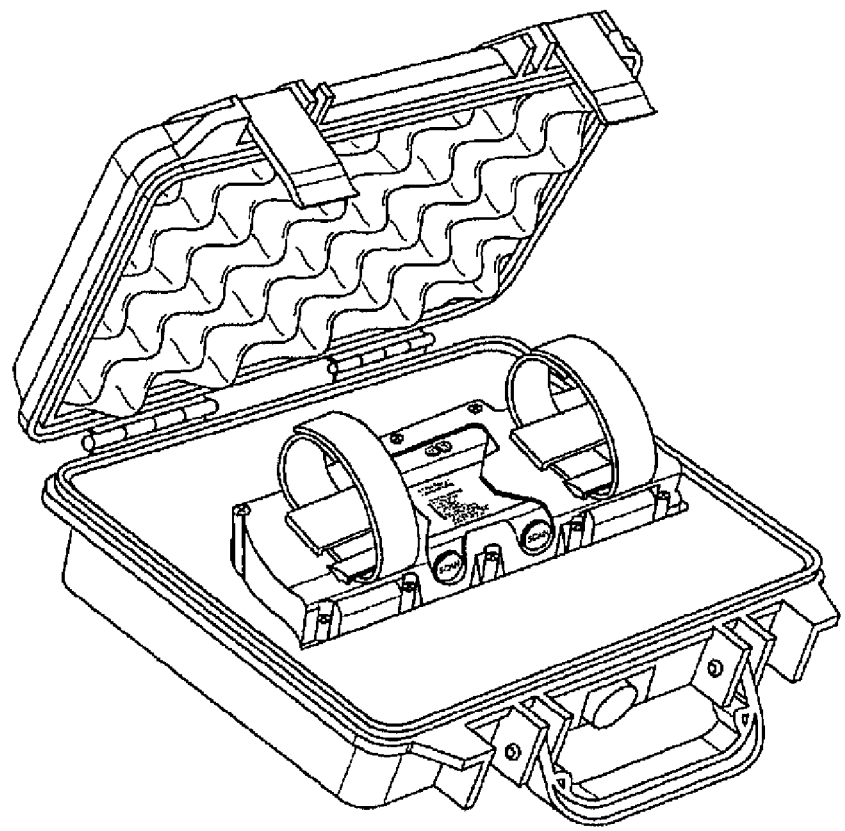
FIG. 10B is a picture of a handheld stepped-frequency scanning device in a case.

Referring to FIGS. 10A and 10B, the compact WPPDS package enables single-handed operation while providing robust protection for the intended application. The unit may also be attached to the forearm or upper arm via straps. FIG. 10A is a picture of a handheld stepped-frequency scanning device relative to a SAW ammo pouch. The housing layout is able to be configured with three circuit card assemblies (CCA), which enables an optional integrated battery recharging circuit, such as a generally commercially available integrated battery recharging circuit. The miniature cavity-backed spiral antennas each contain a planar feed assembly that connects directly to the RF CCA. The Digital CCA contains the DSP as well as the power supply (PS) circuitry.

FIG. 10B is a picture of a handheld stepped-frequency scanning device in a case. The WPPDS unit and accessories can fit into a standard Pelican™ case for storage and transportation. The packaging provides protection against transportation shock and vibration, environmental protection, and facilitates safe storage and case of handling while in daily use by soldiers or rescuers. The case includes compartments for storing arm straps, extra batteries, and an optional vehicle-compatible battery recharger.

To deploy, the operator may hold the device by the straps or by the sides of the unit, affix the unit to either arm via the straps (forearm or upper arm), or mount the device to a pole or tripod (pole/tripod not provided with unit). A standard video camera mount may be connected to the bottom of the unit to facilitate mounting to a tripod or pole. The housing design also features raised stiffener ridges on the front that may facilitate temporary wall mounting using putty. Other implementations may not include the straps, enabling users to operate the device without connecting it to their person.

The housing is made of impact-resistant ABS plastic to help provide protection if the case is dropped or collides with hard objects that may occur during training exercises or during operation, such as on a battlefield or in a rescue operation. The external design of the housing incorporates human factor features to simplify operation in difficult environments. A rubber shield protects the front of the unit. Rubber grip pads are also provided in four areas to facilitate slip-free handheld operation. Multiple SCAN switches support a variety of operational situations.

Figure 11A:
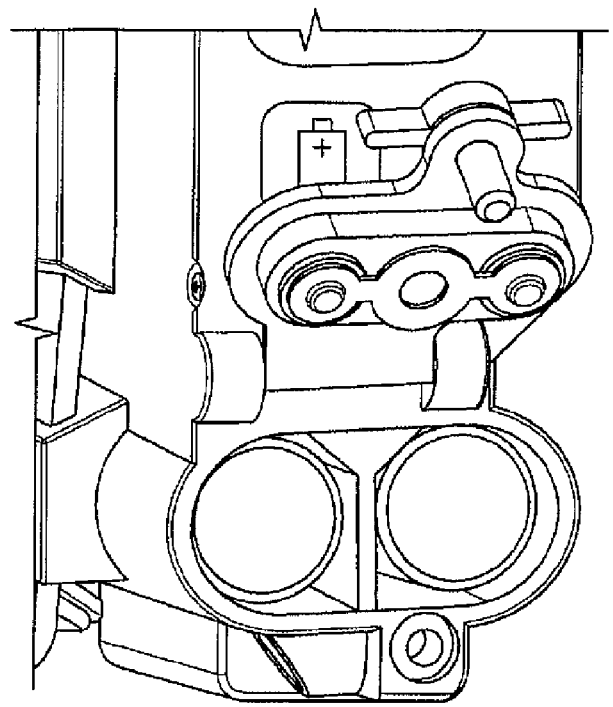
FIG. 11A is a picture illustrating battery access in a handheld stepped-frequency scanning device.
Figure 11B:
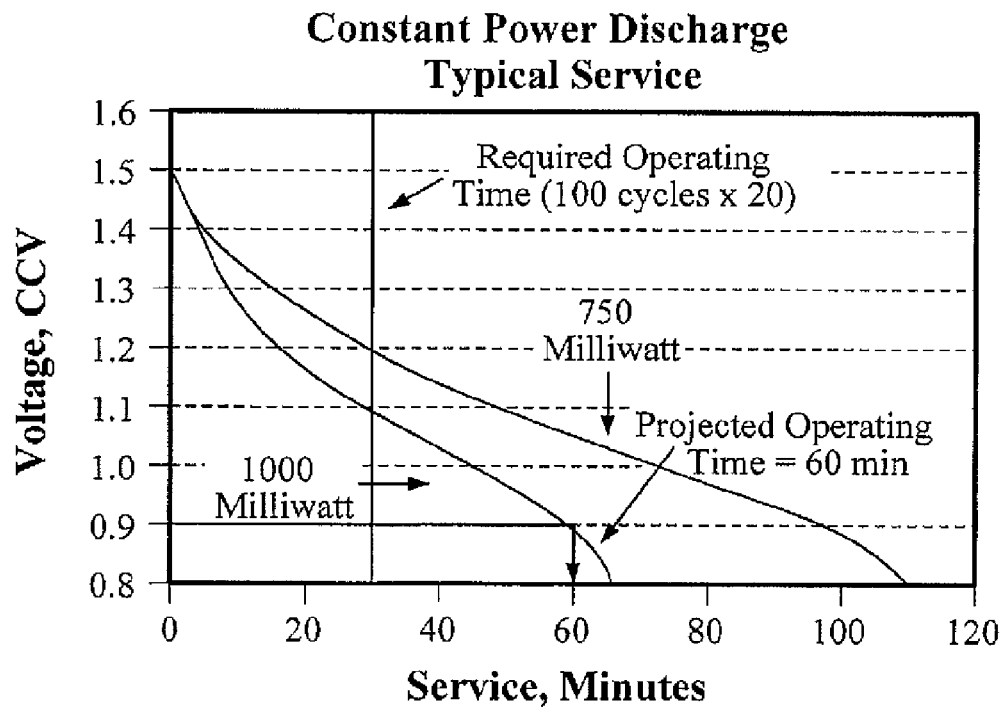
FIG. 11B is a graph illustrating power discharge characteristics in a handheld stepped-frequency scanning device.

FIG. 11A is a picture illustrating battery access in a handheld stepped-frequency scanning device. The battery holder assembly features all eight batteries in the same orientation for easy installation under low light/time critical conditions. The total power draw from batteries can be 2.2 W. In one implementation, four batteries are connected in series, and 2 sets of 4 batteries in parallel. This provides 6V and divides the power by the 2 battery sets. FIG. 11B is a graph illustrating power discharge characteristics in a handheld stepped-frequency scanning device. During run time the individual battery voltage is allowed to decay from 1.4V to 0.9V, providing approximately 1 hour of operation time.

Figure 12A:
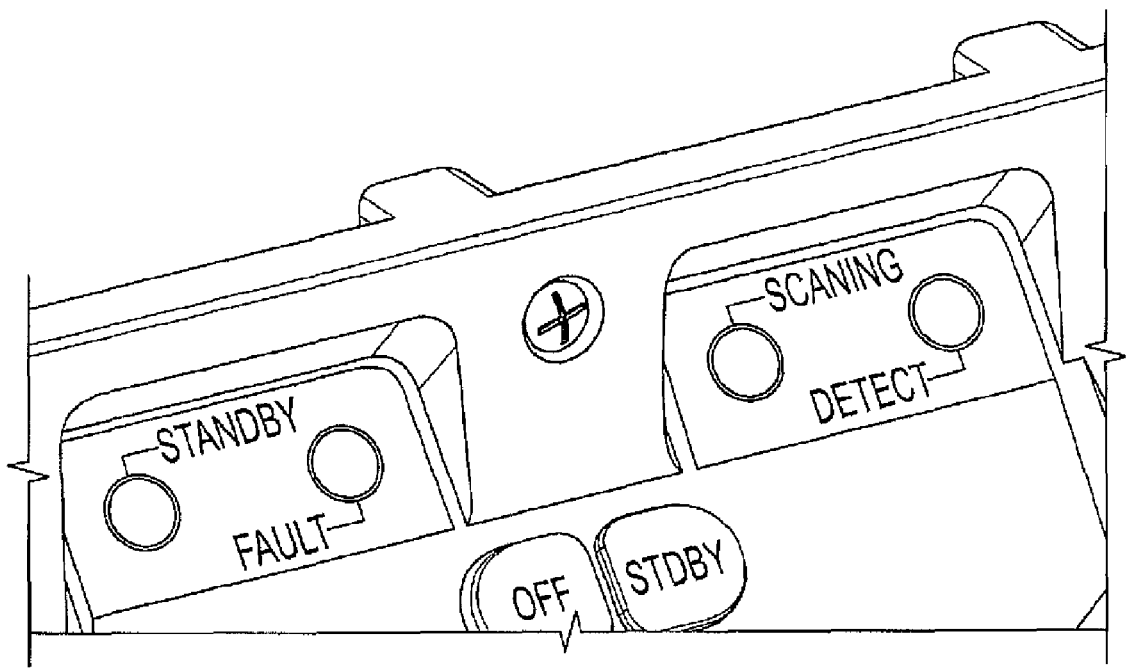
FIG. 12A is a picture illustrating recessed light emitting diodes in a handheld stepped-frequency scanning device.
Figure 12B:
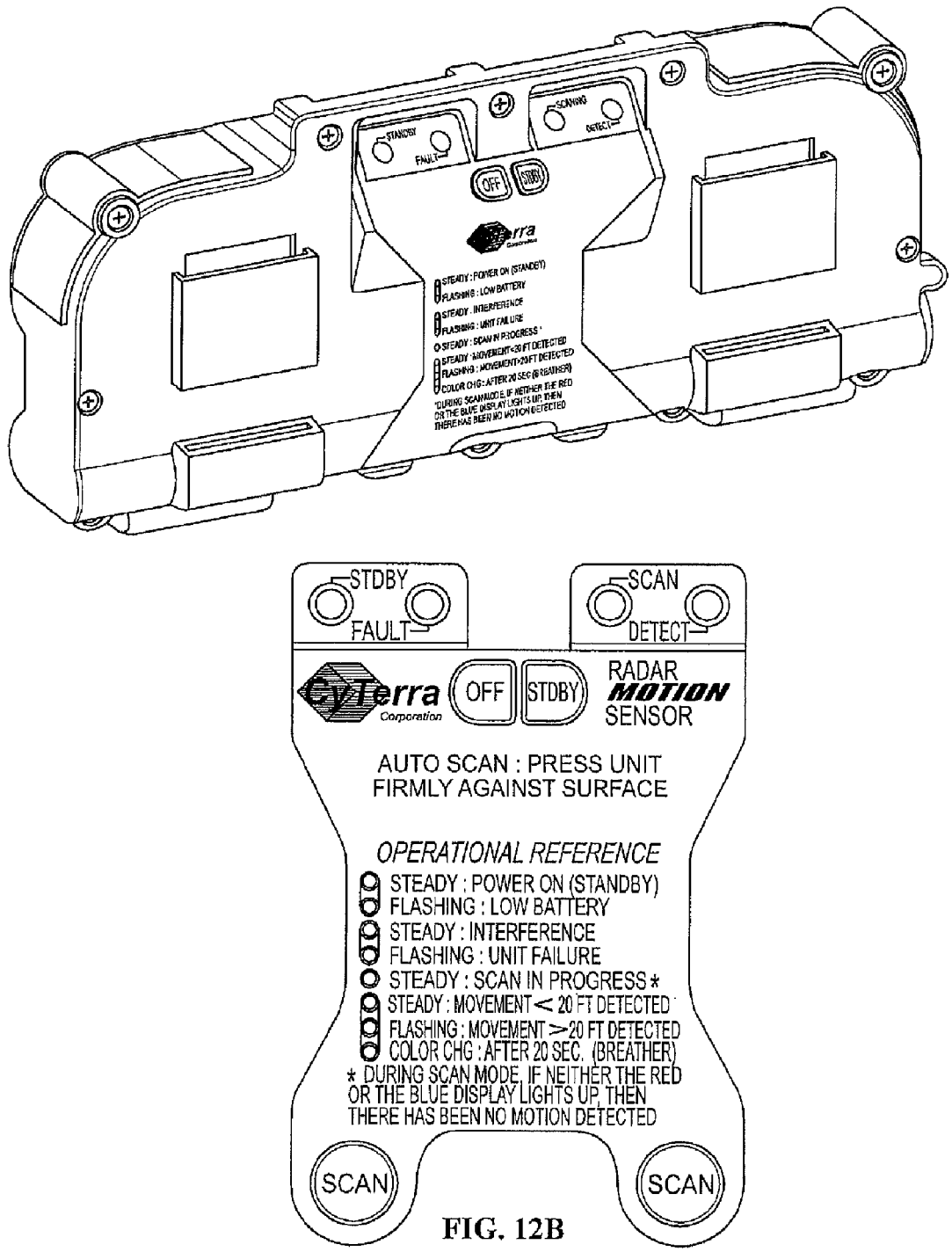
FIG. 12B is a picture illustrating operational controls of a handheld stepped-frequency scanning device.

FIG. 12A is a picture illustrating recessed light emitting diodes in a handheld stepped-frequency scanning device. The device can include light emitting diodes (LEDs) recessed to provide shadowing to enhance daytime vision with or without a display screen (not shown). FIG. 12B is a picture illustrating operational controls of a handheld stepped-frequency scanning device. Power of the device can be affected through use of the OFF and STDBY controls. In Standby mode the circuitry is placed in a power-save mode, and activation of any one of three SCAN pressure switches (one front, two bottom) initiates immediate sensor operation. The device returns to standby mode when the SCAN button is released. Other implementations may include other interface arrangements. For example, a combination of two SCAN switches could be simultaneously pressed (but not held) to enable timed operation, such as when the unit is temporarily adhered to or leaned against a wall, or mounted to a tripod, for hands-off operation.

In one implementation simplifying design, four color LEDs are used to provide indications to the operator without a display screen. The yellow STANDBY LED indicates power status: steady illumination indicates power is on; flashing LED indicates low battery power. The red FAULT LED indicates one of several conditions: steady illumination indicates that the device is unable to make an accurate measurement due to metal blockage, electromagnetic interference (e.g., jamming), or excessive motion of the sensor; flashing illumination indicates a built-in-test (BIT) failure. The green SCANNING LED remains illuminated while the unit is operating to detect motion. The blue DETECT LED indicates that motion has been detected. Steady illumination indicates personnel motion detection at a closer distance. A flashing DETECT LED indicates personnel motion detection at a farther distance. A change in color for the blue DETECT (to Magenta) indicates that subtle movement has been detected.

The device may be powered on and placed in standby mode by momentarily pressing the STDBY switch. The device may be powered off by simultaneously pressing the STDBY and OFF switches. This may prevent accidental power-down during normal operation should the OFF switch get accidentally bumped. In STDBY mode, circuitry is activated in power-save mode, and the device may be immediately operated by pressing one of the SCAN switches. The front SCAN switch may be activated by pressing and holding the device against the wall to be penetrated. One of two bottom SCAN switches may be activated by squeezing with the thumb (normal device orientation) or index finger (inverted orientation), or by pressing the device against the knee or thigh when in a kneeling position.

When any SCAN switch is depressed, the green SCAN LED may illuminate, and may remain illuminated as long as the SCAN switch is depressed. This may alert the operator that the device is operational (i.e., that the SCAN switch is properly depressed). A blue DETECT LED may be used to alert the operator of detected personnel. The device may also be programmed to detect subtle movement. This mode may be initiated by pressing any SCAN switch twice in rapid succession. The green SCAN LED may pulsate slowly when this mode is active. The blue DETECT LED may illuminate when slow movement (respiration) is detected. Some implementations use alternative manners of communicating information to users. For example, one implementations uses a light emitting diode screen to render a two digit number to express a distance of detected moving objects. Other implementations use more sophisticated screens (e.g., more advanced light emitting diodes, organic light emitting diodes, etc.) to render three dimensional representations and more complex information.

Some implementations not employing interferometric processing can have conical radiation patterns so the device may be arbitrarily oriented (within the plane of the wall); i.e., when held against the wall, the unit may be oriented horizontally, vertically, or in any other position without impacting operational performance. The device may also be held off the wall (standoff), provided it is held still during SCAN operation.

Although the techniques and concepts have generally been described in the context of a handheld stepped-frequency scanning device and/or WPPDS, other implementations are contemplated, such as a vehicle-mounted stepped-frequency device.

Other implementations are within the scope of the following claims.

What is claimed is:

1. A method for determining a motion of a system, the method comprising:
   transmitting a stepped-frequency radar signal through a wall to a region on an opposite side of the wall;
   detecting reflections of the transmitted signal with an antenna;
   generating data including information associated with frequency and phase shifts between the transmitted signal and the detected reflections of the transmitted signal;
   analyzing the generated data to determine a first apparent phase of an object in the region;
   transmitting a second stepped-frequency radar signal through the wall;
   detecting reflections of the second transmitted signal with the antenna;
   generating second data including information associated with frequency and phase shifts between the second transmitted signal and the reflections of the second transmitted signal;
   analyzing the generated data to determine a second apparent phase of the object;
   comparing the first apparent phase of the object to the second apparent phase of the object; and
   determining a motion of a system that includes the antenna based on the comparison information associated with a moving object located beyond the second side of the wall, the analyzing including using the determined one or more characteristics of the motion of the transmitted signal and the reflections of the transmitted signal.

2. The method of claim 1 wherein determining the motion of the system includes receiving an indication of the motion of the system from a motion sensor included in the system.

3. The method of claim 2 wherein receiving an indication of the motion of the system from the motion sensor includes receiving information from a global positioning system sensor.

4. The method of claim 2 wherein receiving an indication of the motion of the system from the motion sensor includes receiving information from one or more sensors.

5. The method of claim 4 wherein receiving information from the one or more sensors includes receiving information from a global positioning system (GPS) sensor and from an inertial sensor and sampling one or more outputs of the inertial sensor indicating a current state of acceleration in each of three spatial dimensions.

6. The method of claim 2 wherein generating the data includes generating packets of data that each include information associated with the received indication of the motion of the system and the information associated with frequency and phase shifts.

7. The method of claim 2 further comprising: using the determined motion of the system to compensate for the effect of the motion by
altering the generated data to reverse the Doppler shift of the detected reflections resulting from the determined motion of the system, and analyzing the altered data to determine information associated with a moving object located beyond the second side of the wall.

8. The method of claim 1 further comprising identifying a phase change of detected reflections of the transmitted signal from stationary objects wherein:
the motion of the system is determined based on the identification of the phase change of detected reflections of the transmitted signal from stationary objects.

9. The method of claim 8 further comprising using the determined motion of the system to compensate for the effect of the motion by
altering the generated data to reverse the Doppler shift of the detected reflections resulting from the motion of the system, and analyzing the altered data to determine the information associated with a moving object located beyond the second side of the wall.

10. The method of claim 1 wherein the motion of the system is determined based on identifying phase changes that indicate a pattern of movement of objects.

11. The method of claim 1 wherein:
transmitting the stepped-frequency radar signal includes beginning transmission of the stepped-frequency radar signal at a first system location and moving the system during transmission of the stepped-frequency radar signal from the first system location to a second system location;
detecting reflections of the transmitted signal with the antenna while the antenna is in motion includes detecting reflections of the transmitted signal during the movement of the antenna from the first system location to the second system location; and
analyzing the generated data includes determining the information associated with the moving object located beyond the second side of the wall based upon the reflections detected during the movement of the antenna from the first system location to the second system location.

12. The method of claim 11 wherein:
generating the data includes generating data for detected reflections which includes information associated with frequency and phase shifts and associated with the motion of the system determined during the detection of reflections of the transmitted signal; and
analyzing the generated data includes generating a synthetic aperture radar image using the data including information associated with frequency and phase shifts and associated with the motion of the system.

13. The method of claim 12 wherein:
determining the motion of the system during the detection of reflections of the transmitted signal includes sampling output of an inertial sensor within the system; and
generating the data includes generating a packet of data for reflections received at each of multiple system locations between the first and second system locations, each packet including the information associated with frequency and phase shifts, and output of the sampled inertial sensor at the time the reflection was detected.

14. The method of claim 1 further comprising:
identifying a transmit-to-receive leakage signal resulting from the transmission of the stepped-frequency radar signal;
generating a cancellation waveform configured to remove effects of the identified transmit-to-receive leakage signal; and
using the generated cancellation waveform to remove effects of transmit-to-receive leakage signal of subsequent transmissions.

15. The method of claim 1 further comprising:
after transmitting the stepped-frequency radar signal, determining that the stepped-frequency radar signal should be altered;
generating an altered stepped-frequency radar signal such that the order of the transmitted frequencies is changed or such that one or more of the transmitted frequencies is removed; and
transmitting the altered stepped-frequency radar signal.

16. The method of claim 1 wherein determining the motion of the system includes determining the motion of the antenna.

17. The method of claim 1, further comprising:
adjusting the generated data to account for the determined motion of the system.

18. The method of claim 1, further comprising altering frequency data to account for the determined motion of the system.

19. The method of claim 1, wherein the object comprises a stationary object.

20. The method of claim 1, wherein the object comprises the wall.

21. The method of claim 1, wherein the object comprises multiple objects, the first apparent phase comprises a first apparent phase for each of the multiple objects, the second apparent phase comprises a second apparent phase for each of the multiple objects; and further comprising:
analyzing each of the phases of the first apparent phase to determine a first pattern of apparent motion of the multiple objects; and
analyzing each of the phases of the second apparent phase to determine a second pattern of apparent motion of the multiple objects, wherein the comparison comprises a comparison of the first and second patterns of motion.

22. The method of claim 1, wherein the transmitted stepped-frequency radar signal and the second transmitted stepped-frequency radar signal are below 4 GHz.

23. A system comprising:
transmission circuitry configured to enable transmission, through a wall to a region, of a stepped-frequency radar signal and a second stepped-frequency radar signal;
an antenna configured to detect reflections of the transmitted signal and reflections of the second transmitted signal;
receiving circuitry configured to receive detected reflections from the antenna and to generate data including information associated with frequency and phase shifts between the transmitted signal and the reflections of the transmitted signal, and to generate second data including information associated with frequency and phase shifts between the second transmitted signal and the second detected reflection; and a processor configured to receive the generated data from the receiving circuitry and to:
analyze the generated data to determine a first apparent phase of an object in the region;
analyze the second generated data to determine a second apparent phase of the object;
compare the first apparent phase of the object to the second apparent phase of the object; and
determine a motion of the system based on the comparison.

24. The system of claim 23 wherein the receiving circuitry is a part of the processor.

25. The system of claim 23 further comprising a motion sensor configured to provide an indication of the motion of the system, and wherein,
to generate the data, the receiving circuitry is configured to receive the indication of the motion of the system from the motion sensor.

26. The system of claim 25 wherein the motion sensor is a global positioning system sensor.

27. The system of claim 25 wherein the motion sensor is an inertial sensor.

28. The system of claim 27 wherein the inertial sensor is configured to output a current state of acceleration in each of three spatial dimensions.

29. The system of claim 27 wherein to generate the data, the receiving circuitry is configured to generate packets of data which each include information associated with the received indication of the determined motion of the system along with the information associated with frequency and phase shifts.

30. The system of claim 23 wherein the processor is further configured to use the determined motion of the system to compensate for the effect of the motion by
altering the generated data to reverse the Doppler shift of the detected reflections resulting from the motion of the system, and analyzing the altered data to determine information associated with a moving object located in the region.

31. The system of claim 23 wherein the processor is further configured to use the determined motion of the system to compensate for the effect of the motion by identifying a phase change of detected reflections of the transmitted signal from stationary objects, and
determining the motion of the system based on the identification of the phase change of detected reflections of the transmitted signal from stationary objects.

32. The system of claim 31 wherein, to use the determined motion of the system to compensate for the effect of the motion, the processor is configured to:
alter the generated data to reverse the Doppler shift of the detected reflections resulting from the determined motion of the system; and
analyze the altered data to determine the information associated with a moving object on the side of the wall different than the side of the wall of which the system is located.

33. The system of claim 23 wherein, the motion of the system is determined by identifying phase changes indicative of a pattern of movement of objects.

34. The system of claim 23 wherein:
the transmission circuitry is configured to enable the transmission of the stepped-frequency radar signal to begin at a first system location and to continue during movement of the system from the first system location to a second system location;
the receiving circuitry is configured to receive the detected reflections of the first transmitted signal during the movement of the system from the first system location to the second system location; and
the processor is configured to determine the information associated with a moving object located at the side of the wall different than the side of the wall of which the system is located based upon the reflections detected during the movement of the system from the first system location to the second system location.

35. The system of claim 34 wherein:
to generate the data, the receiving circuitry is configured to generate data for detected reflections that includes information associated with frequency and phase shifts and information associated with the motion of the system; and
to analyze the generated data, the processor is configured to generate a synthetic aperture radar image using the data including information associated with frequency and phase shifts and the motion of the system.

36. The system of claim 35 further comprising an inertial sensor configured to determine the motion of the system wherein,
to generate the data, the receiving circuitry is configured to sample output of the inertial sensor and to generate a packet of data for reflections received at multiple system locations between the first and second system locations, each packet including the information associated with frequency and phase shifts, and output of the sampled inertial sensor at the time the reflection was detected.

37. The system of claim 23 wherein the processor is configured to:
identify a transmit-to-receive leakage signal resulting from the transmission of the stepped-frequency radar signal;
generate a cancellation waveform configured to remove effects of the identified transmit-to-receive leakage signal; and
use the generated cancellation waveform to remove effects of transmit-to-receive leakage signal of subsequent transmissions.

38. The system of claim 23 wherein the processor is configured to:
after the transmission of the stepped-frequency radar signal, determine the stepped-frequency radar signal should be altered;
enable generation of the altered stepped-frequency radar signal such that the order of the transmitted frequencies is changed or such that one or more of the transmitted frequencies is removed; and
enable the transmission circuitry to transmit the altered stepped-frequency radar signal.

39. The system of claim 23 wherein, to use the motion of the system, the processor is configured to use one or more characteristics of motion of the antenna.

* * * * *

UNITED STATES PATENT AND TRADEMARK OFFICE
CERTIFICATE OF CORRECTION

PATENT NO.         : 8,362,942 B2
APPLICATION NO.    : 12/391940
DATED              : January 29, 2013
INVENTOR(S)        : James McNeill, Todd Mackey and Tim Dyson Page 1 of 1

It is certified that error appears in the above-identified patent and that said Letters Patent is hereby corrected as shown below:

In the claims

In Claim 1, at Column 32, line 56, replace "comparison information associated with a moving object located beyond the second side of the wall, the analyzing including using the determined one or more characteristics of the motion of the transmitted signal and the reflections of the transmitted signal" with --comparison.--.

Signed and Sealed this
Fifteenth Day of December, 2015

Michelle K. Lee
*Director of the United States Patent and Trademark Office*